United States Patent [19]

Dodakian

[11] Patent Number: 5,295,490
[45] Date of Patent: Mar. 22, 1994

[54] SELF-CONTAINED APNEA MONITOR

[76] Inventor: Wayne S. Dodakian, 77 Oakland Ave., New Britain, Conn. 06053

[21] Appl. No.: 6,829

[22] Filed: Jan. 21, 1993

[51] Int. Cl.⁵ .............................................. A61B 5/113
[52] U.S. Cl. ....................................... 128/721; 128/782
[58] Field of Search ................................... 128/721-3, 128/774-775, 778, 780, 782, 716; 340/573, 575

[56] References Cited

U.S. PATENT DOCUMENTS

| | | |
|---|---|---|
| 3,638,642 | 2/1972 | Heflin, Sr. . |
| 3,713,436 | 1/1973 | Hardway, Jr. . |
| 3,782,368 | 1/1974 | Reibold ............................ 128/721 X |
| 3,786,495 | 1/1974 | Spence . |
| 3,798,629 | 3/1974 | De La Taillade et al. . |
| 3,802,417 | 4/1974 | Lang . |
| 3,809,828 | 5/1974 | Haugsjaa et al. . |
| 3,882,847 | 5/1975 | Jacobs . |
| 3,890,511 | 6/1975 | Haugsjaa et al. . |
| 3,894,243 | 7/1975 | Edelman et al. . |
| 3,898,981 | 8/1975 | Basham . |
| 3,926,177 | 12/1975 | Hardway, Jr. et al. . |
| 3,996,922 | 12/1976 | Basham . |
| 4,121,573 | 10/1978 | Crovella et al. . |
| 4,146,885 | 3/1979 | Lawson, Jr. . |
| 4,202,350 | 5/1980 | Walton . |
| 4,213,348 | 7/1980 | Reinertson et al. . |
| 4,258,720 | 3/1981 | Flowers . |
| 4,289,142 | 9/1981 | Kearns . |
| 4,350,166 | 9/1982 | Mobarry . |
| 4,365,636 | 12/1982 | Barker . |
| 4,381,788 | 5/1983 | Douglas ............................ 128/782 X |
| 4,406,290 | 9/1983 | Walbeoffe-Wilson et al. . |
| 4,414,982 | 11/1983 | Durkan . |
| 4,417,589 | 11/1983 | Favaloro . |
| 4,433,693 | 2/1984 | Hochstein . |
| 4,444,201 | 4/1984 | Itoh . |
| 4,456,015 | 6/1984 | Sackner . |
| 4,475,559 | 10/1984 | Horn . |
| 4,478,224 | 10/1984 | Bailey . |
| 4,506,678 | 3/1985 | Russell et al. . |
| 4,509,527 | 4/1985 | Fraden . |
| 4,546,778 | 10/1985 | Sullivan . |
| 4,576,149 | 3/1986 | Manus et al. . |
| 4,580,575 | 4/1986 | Birnbauam et al. . |
| 4,595,016 | 6/1986 | Fertig et al. . |
| 4,625,733 | 12/1986 | Saynajakangas . |
| 4,630,614 | 12/1986 | Atlas . |
| 4,648,396 | 3/1987 | Raemer . |
| 4,671,297 | 6/1987 | Schulze, Jr. . |
| 4,696,307 | 9/1987 | Montgieux ............................ 128/782 X |
| 4,838,279 | 6/1989 | Fore ............................ 128/782 X |
| 4,846,462 | 7/1989 | Regnier et al. ............................ 128/721 X |
| 4,895,162 | 1/1990 | Dolliver ............................ 128/802 X |
| 4,989,612 | 2/1991 | Fore ............................ 128/782 X |
| 5,107,855 | 4/1992 | Harrington et al. ............................ 128/721 |

Primary Examiner—Angela D. Sykes
Attorney, Agent, or Firm—Price, Gess & Ubell

[57] ABSTRACT

The self-contained apnea monitor of the invention detects an apnea event or shallow breathing in a patient such as an infant, and generates an audible and visual alarm in response thereto. The monitor includes an elastic fabric belt for snugly encircling the abdomen or chest of an infant and a detector unit for detecting expansion or contraction of the elastic fabric belt caused by respiration. To this end, the belt includes a helical spring extending along its length. An inextensible wire is provided within the spring connecting a remote end of the spring to the detector unit. Thus configured, respiration of the infant causes the wire to be withdrawn from the detector unit. Within the detector unit, the wire is mounted to a recoil spring assembly which provides a biasing force for recoiling the wire subsequent to respiration. A detecting arm or magnet is mounted to a barrel containing the recoil spring within an electrical circuit provided to detect motion of the detecting arm or magnet. The electrical circuit measures a time interval between consecutive respirations and generates an audible alarm if the time interval exceeds a predetermined period of time.

44 Claims, 18 Drawing Sheets

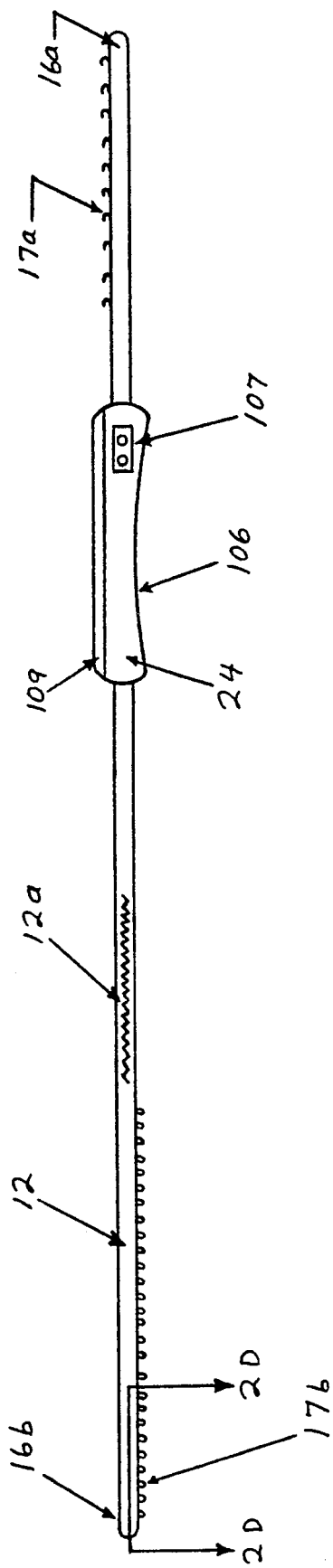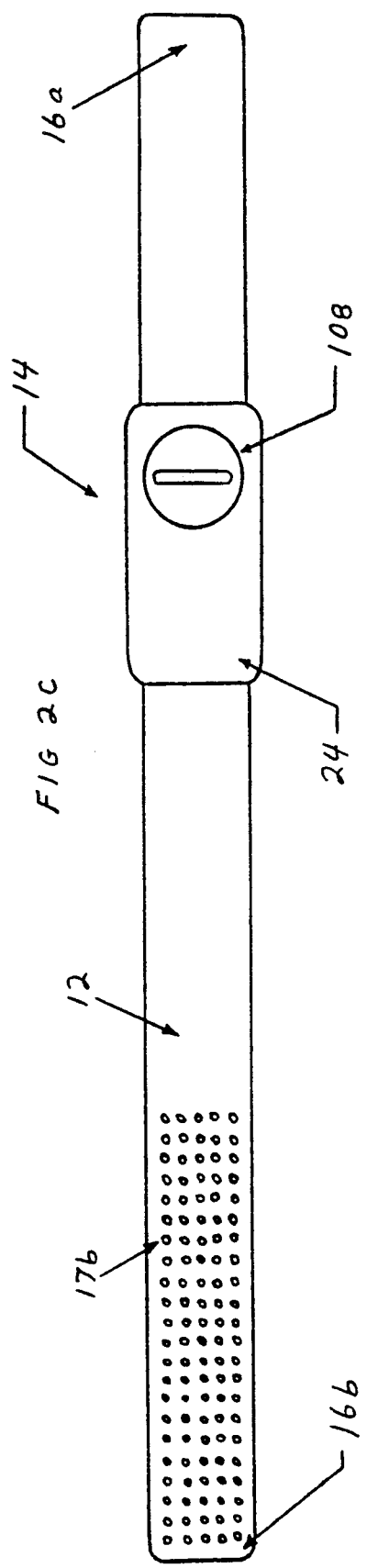
FIG 2B
FIG 2C

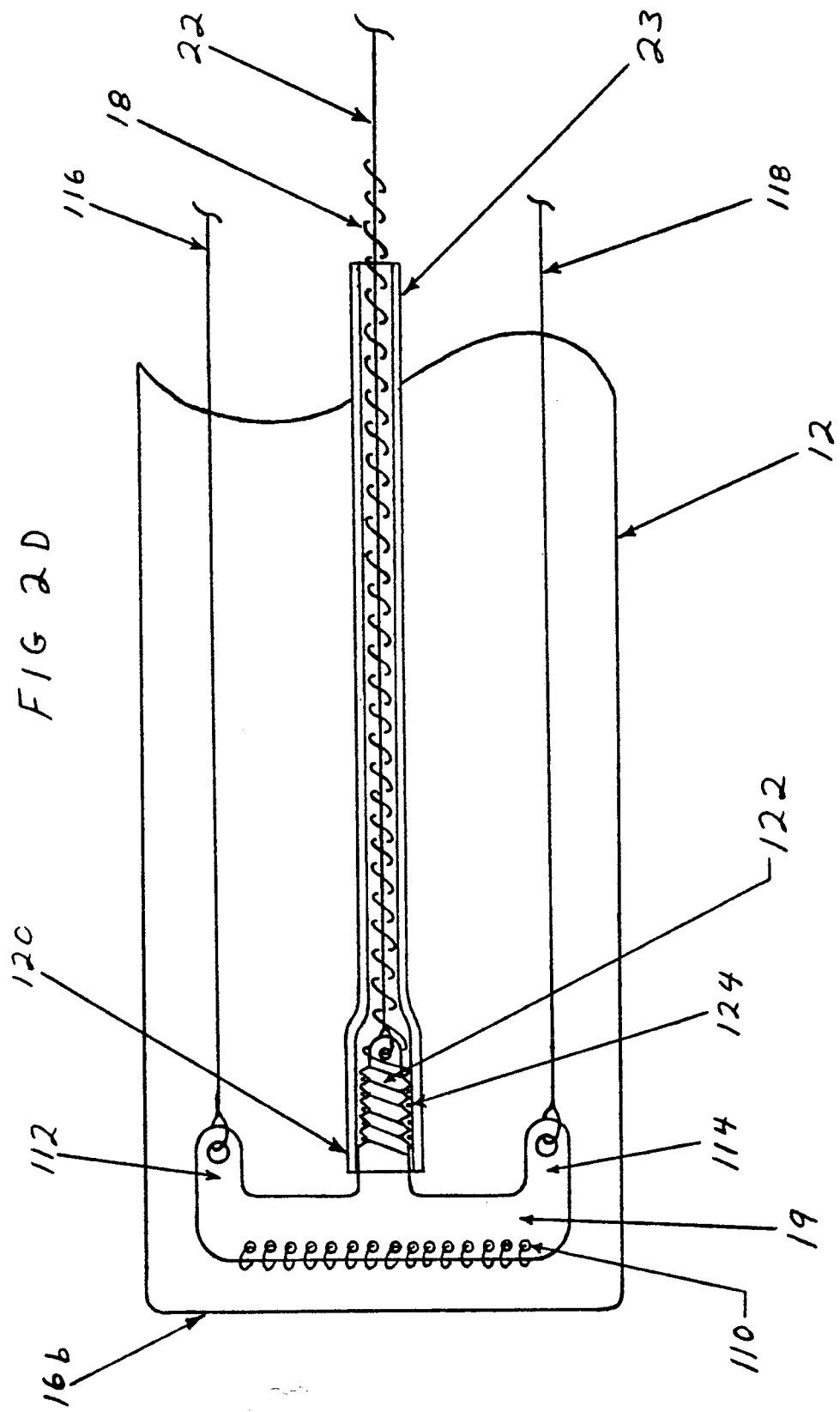

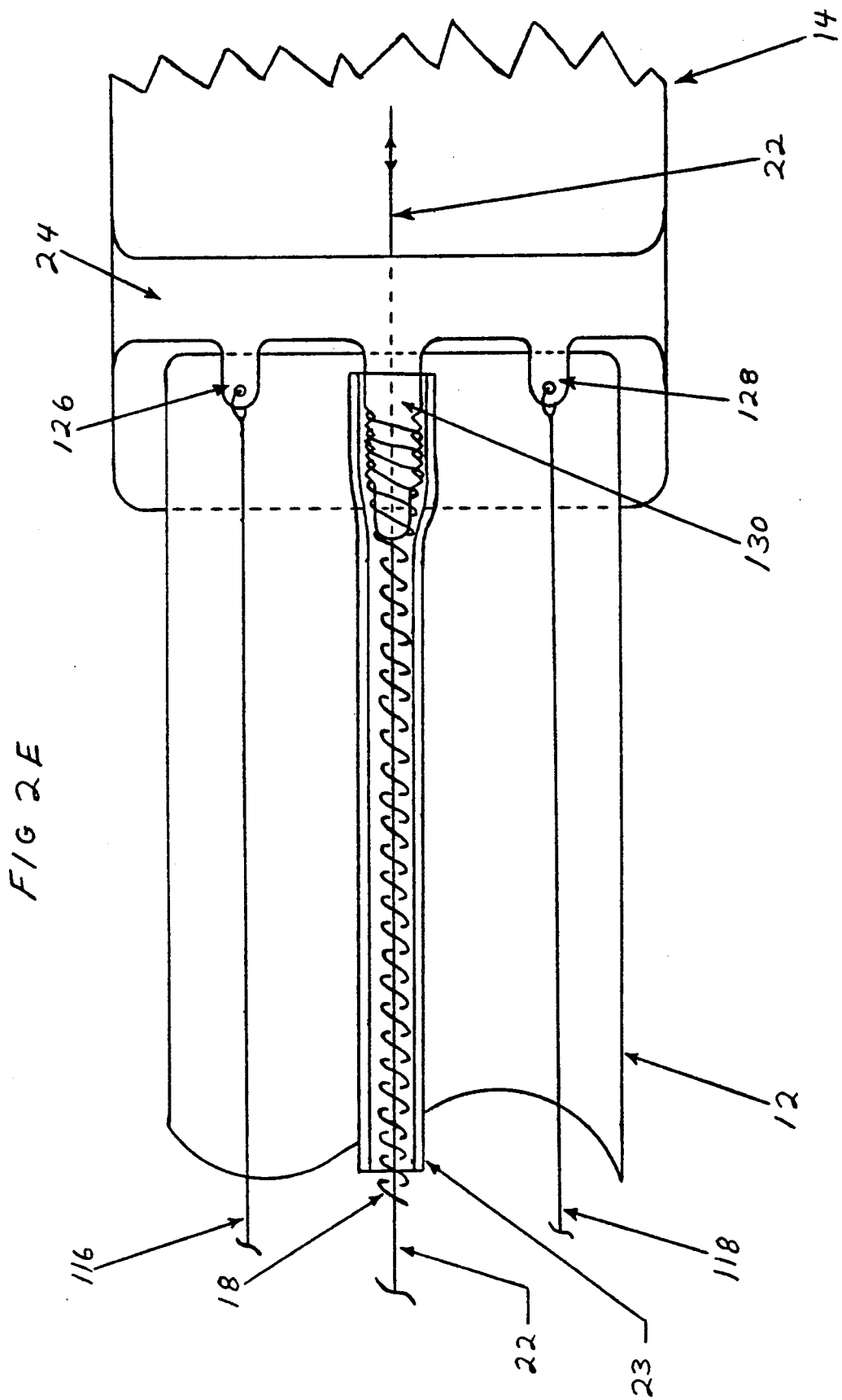

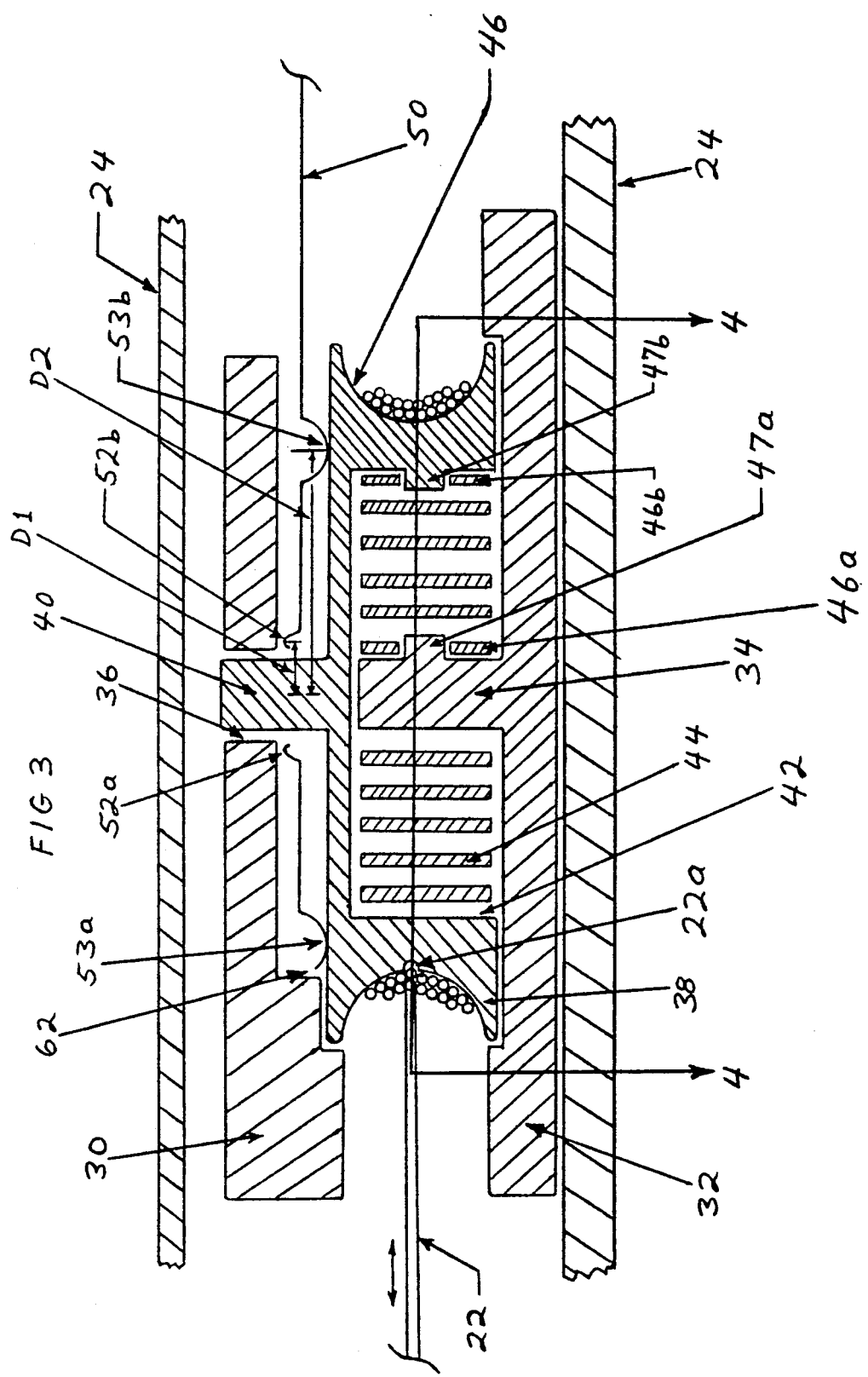

1

SELF-CONTAINED APNEA MONITOR

BACKGROUND OF THE INVENTION

1. Field of the Invention

The invention relates generally to respiration monitors and, in particular, to a self-contained apnea monitor for use at home or in a hospital.

2. Description of Related Art

Apnea, the transient cessation of breathing, is a significant health problem. Apnea most often occurs during sleep and is often undetected. Apnea during sleep is commonly called "sleep apnea."

In a mild form of sleep apnea, a person temporarily stops breathing during the night, often several times. Each individual instance of a cessation of breathing is referred to as an "apnea event," and such events are deemed to occur when breathing stops for at least 20–35 seconds.

Left untreated, mild sleep apnea can result in, e.g, excessive tiredness during the day, an irregular heartbeat at night, anxiety, depression, or an inability to concentrate, including a possible loss of memory. In its more serious forms, sleep apnea can result in death, particularly for infants. Recent research has shown that apnea may be a leading cause of Sudden Infant Death Syndrome.

Generally, sleep apnea takes three forms: obstructive sleep apnea, central sleep apnea, and mixed sleep apnea. In obstructive sleep apnea, structures in the throat block the flow of air to and from the lungs, or the obstruction may be caused by a foreign object lodged within the airway. Central sleep apnea occurs when the brain does not send out necessary signals to continue breathing, i.e., the person simply "forgets" to breathe. Mixed sleep apnea is a combination of both obstructive sleep apnea and central sleep apnea.

Another breathing phenomena, closely related to apnea, is "periodic breathing" or "shallow breathing." Shallow breathing occurs due to a lack of breathing volume over an extended period of time, perhaps 15–20 minutes or more. Due to a lack of adequate breathing volume, blood oxygen saturation levels become depleted, leading to a "hypoxic" state. With apnea, breathing merely ceases, quickly leading to hypoxia. With shallow breathing, oxygen depletion is more gradual. Many conventional apnea monitors are not equipped to detect hypoxia resulting from shallow breathing.

Numerous devices have been designed to detect apnea events, either for the purpose of diagnosis or for the purpose of alerting a physician or parent that an apnea event is occurring such that the patient may be revived as necessary. Such devices detect or measure one or more aspects of breathing including: respiration, heart rate, oxygenation or ventilation. Respiration monitors detect either actual airflow to and from the lungs by means of a mouth or nasal thermistor, or by means of a carbon dioxide detector. Alternatively, the monitors detect an effort at breathing by means of electrical activity sensors having electrodes for measuring skin impedance or inductance. Heart rate is typically measured using a continuous ECG or a cardio-tachometer. Oxygenation and ventilation are detected through transcutaneous oxygen tension and saturation and transcutaneous carbon dioxide, respectively.

Exemplary respiration monitors are disclosed in U.S. Pat. No. 4,576,179 to Manus et al., U.S. Pat. No. 4,433,693 to Hochstein, and U.S. Pat. No. 3,782,368 to Reibold.

Manus et al. discloses a respiration monitoring apparatus mounted on a belt for encircling the thorax of a patient. A piezoelectric crystal is mounted within the device such that outward extension of the thorax causes a bending or deformation of the piezoelectric crystal, thus producing an electrical signal which is monitored.

Hochstein also discloses a respiration monitoring device mounted on a belt for encircling the thorax of a patient. The device includes an oscillator for generating an electromagnetic field having an output frequency in the radiofrequency range, and further includes a high Q passively-tuned LC circuit, which has a resonant frequency variable in the radiofrequency range generated by the oscillator. These devices are positioned on the belt encircling the patient's thorax such that expansion of the thorax varies the resonant frequency of the LC circuit. Extension of the thorax is thus detected when the resonant frequency of the LC circuit corresponds with the frequency of the electromagnetic field generated by the oscillator.

Reibold discloses a monitor including a moment actuated transducer unit mounted to an elastic belt for encircling the thorax of a patient. The moment-actuated transducer includes a piezoelectric element having a predetermined capacitance. The piezoelectric element is connected to the belt by a pair of bending arms such that expansion of the thorax bends the bending arms and, thus, deforms the piezoelectric element. Means are provided to detect an electrical signal output from the piezoelectric element.

Related devices are disclosed in U.S. Pat. No. 3,996,922 to Basham, U.S. Pat. No. 3,638,642 to Heflin, Sr., U.S. Pat. No. 4,630,614 to Atlas, U.S. Pat. No. 4,671,297 to Schulze, Jr., U.S. Pat. No. 4,648,396 to Raemer, U.S. Pat. No. 4,580,575 to Birnbaum et al.. U.S. Pat. No. 4,625,733 to Säynäjäkangas, U.S. Pat. No. 4,595,016 to Fertig et al., U.S. Pat. No. 4,546,778 to Sullivan. U.S. Pat. No. 4,509,527 to Fraden. U.S. Pat. No. 4,506,678 to Russell et al.. U.S. Pat. No. 4,478,224 to Bailey, U.S. Pat. No. 4,475,559 to Horn, U.S. Pat. No. 4,444,201 to Itoh, U.S. Pat. No. 4,417,589 to Favaloro. U.S. Pat. No. 4,414,982 to Durkan. U.S. Pat. No. 4,365,636 to Barker, U.S. Pat. No. 4,350,166 to Mobarry, U.S. Pat. No. 4,289,142 to Kearns. U.S. Pat. No. 4,146,885 to Lawson, Jr.. U.S. Pat. No. 3,802,417 to Lang, U.S. Pat. No. 3,882,847 to Jacobs, and U.S. Pat. No. 3,713,436 to Hardway, Jr.

The apnea detectors and monitors of the prior art are generally expensive, and may be unreliable, and difficult to use. Many require training to operate and constant supervision to maintain.

SUMMARY OF THE INVENTION

Accordingly, it is an object of the invention to provide an improved apnea detector.

It is further object of the invention to provide a self-contained apnea detector.

It is a further object of the invention to provide an easy-to-use apnea monitor which may be worn around the chest or abdomen of a patient and which does not interfere with the movement of the patient.

It is a further object of the invention to provide a inexpensive and reliable apnea detector to provide an audible and visual alarm if an apnea event occurs.

It is a further object of the invention to provide an apnea detector powered by an uninterruptible power supply with an on-board battery, the detector providing an indication if the battery voltage has fallen below a predetermined level.

It is a further object of the invention to provide a water resistant apnea detector having an alarm which indicates if potentially damaging moisture has penetrated the detector.

It is a further object of the invention to provide an apnea monitor which can be securely but unobtrusively mounted to a patient and which does not hinder the patient's free movement and cannot strangle the patient via entanglement of electrode wires.

It is another object of the invention to provide an apnea detector which monitors the expansion and contraction of a patient's thorax or abdomen and sounds an alarm if no such expansion or contraction is detected for a predetermined minimum time period.

It is a further object to provide such an apnea detector which additionally detects shallow breathing.

These and other advantages of the invention are achieved by providing a monitor for monitoring a patient to detect an apnea event or shallow breathing and for providing an indication responsive thereto, the monitor including belt means for substantially encircling a portion of the body of a patient and for expanding and contracting in response to respiration of the patient, and detection means connecting first and second ends of the belt means for detecting expansion and contraction of the belt means. The belt means includes a substantially inextensible biased wire extending along at least a portion thereof. A first end of the wire is displaceably connected to the detection means and a second end is fixedly connected to the belt means at a location intermediate the first and second ends of the belt means. The wire is displaced outwardly from the detection means upon an expansion of the belt means. The wire is biased to return to a predisplaced configuration upon contraction of the belt means. The detection means detects respiration by detecting displacement of the wire. Measurement means are provided for measuring a time interval between displacements of the wire, and determination means and indication means are provided for, respectively, determining and indicating whether the time interval exceeds a minimum threshold time interval such that an indication is provided of a prolonged period without any detected respiration.

In accordance with a preferred embodiment, the wire is carried within a helical spring. A first end of the spring is fixedly connected to the detection means and a second end is fixedly connected to the belt means at a location intermediate the first and second ends of the belt means. The helical spring is provided to further bias the wire and to isolate the wire such that the wire remains freely and smoothly displaceable so that detection of respiration is not impeded.

In one embodiment, the detection means detects a displacement in the wire by connecting the proximal end of the wire to a rotatable barrel. A sensing arm is mounted to the barrel such that the sensing arm pivots in response to displacement of the wire. A pair of posts are mounted in the path of the sensing arm such that, as the arm pivots back and forth in response to inhalation and exhalation, the sensing arm alternately contacts the posts. The posts are electrically connected with a sensing circuit which detects contact between the sensing arm and the post. In this manner, displacement of the wire caused by breathing is registered as an electrical signal by the electrical circuit.

In an alternative embodiment, a disc magnet is concentrically mounted to the barrel with the magnet in close proximity to an induction loop. As the barrel rotates in response to displacement of the wire, the magnet pivots adjacent to the magnet inductance loop, thereby inducing an electrical current, proportional to the displacement within the loop, which is, in turn, detected by an electrical circuit.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2b is a side view of the apnea monitor of FIG. 1;

FIG. 2c is a bottom view of the apnea monitor of FIG. 1;

FIG. 2d is a top view of one end of the belt of FIG. 2a, shown with internal components exposed;

FIG. 2e is a top view of a portion of the belt and monitor of the apnea monitor of FIG. 2a, shown with internal components of the belt exposed;

FIG. 2f is a cross-sectional view taken along lines 2F—2F of FIG. 2a;

FIG. 3 is a vertical cross-section of a detector unit of the apnea monitor of FIG. 2a;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a self-contained apnea monitor.

Figure 1:
FIG. 1 is a top view of an infant wearing an apnea monitor constructed in accordance with a preferred embodiment of the invention.

Referring to FIG. 1, an apnea and shallow breathing monitor 10 is shown encircling the abdomen of an infant. Apnea monitor 10 includes a belt 12 and a detector unit 14 for detecting expansion and contraction of belt 12 caused by respiration of the infant. Detector unit 14 includes means for measuring time intervals between respirations and means for signalling an audible and visual alarm if no respiration is detected within a specified period. In FIG. 1, the audible alarm is illustrated emanating from detector unit 14.

Figure 2A:
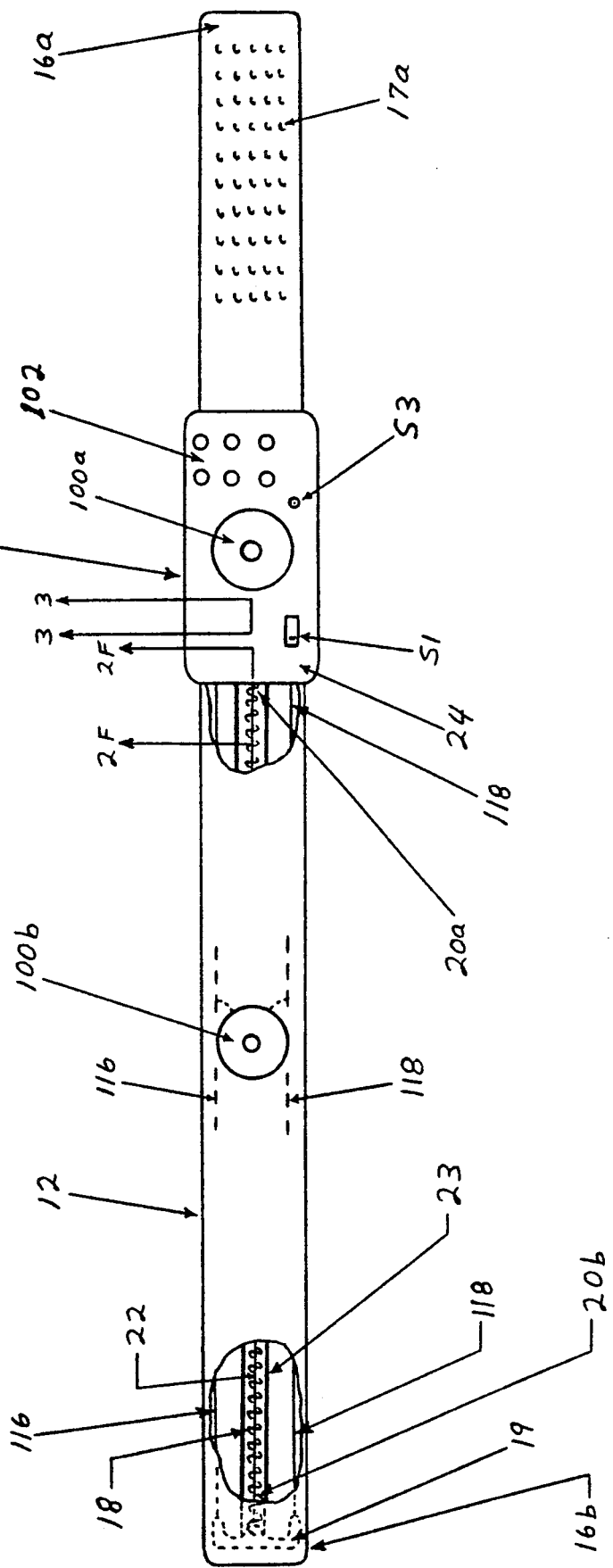
FIG. 2a is a top view of the apnea monitor of FIG. 1.

Referring to FIGS. 2a–2c, apnea monitor 10 is shown unattached to a patient. Belt 12 comprises an elastic fabric adapted to encircle the thorax or abdomen of an infant. Belt 12 includes attachment ends 16a and 16b with the attachment ends provided with a plurality of mating hook 17a and clasp or loop members 17b such as the attachment means sold under the trademark "VELCRO."

More specifically, hook members are provided on a top surface of end 16a and clasp members are provided on a top surface of end 16b such that, with belt 12 encircling an infant, ends 16a and 16b engage, thus securing belt 12 to the infant. The elastic fabric of belt 12 ensures that monitor 10 snugly fits around the infant.

Apnea monitor 10 can be adapted to detect apnea in any respiratory animal, and can be adapted, by providing a belt 12 of suitable length, to encircle any portion of the animal that expands and contracts in response to respiration. However, hereinafter this description will refer only to an apnea monitor for use with a human infant.

Belt 12 includes a helical spring 18 (shown in cutaway in FIG. 2a) having a first end 20a fixedly attached to a housing 24 of detector 14. A second end 20b of spring 18 is fixedly attached to belt 12 at a location intermediate detector housing 24 and attachment end 16a. Preferably, end 20b is attached to end 16b via a termination bar 19 (phantom lines) sewed into attachment end 16b. Termination bar 19 is described in greater detail below with reference to FIG. 2d.

Spring 18 carries within it a substantially inextensible wire 22. Wire 22 is fixedly attached to end 20b of spring 18, and is displaceably connected within housing 24 in a manner described below. An opening 26 is provided on a side of housing 24 to allow wire 22 to extend from spring 18 into housing 24.

In use, belt 12 of monitor 10 is fitted to the abdomen or thorax of an infant and expands and contracts in response to respiration of the infant. As belt 12 expands, spring 18 likewise expands. Since wire 22 is fixedly connected to end 20b of spring 18, wire 22 is drawn out of detector unit 14 during expansion of belt 12. Preferably, wire 22 is coated with a material having a low coefficient of friction such as polytetrafluoroethylene, sold under the trademark "TEFLON." An interior surface of helical spring 18 is also preferably coated with a material having a low coefficient of friction. Thus comprised, wire 22 slides with very little friction within spring 18 as spring 18 is expanded or contracted in response to respiration of the infant.

Spring 18 is completely enclosed within a flexible watertight tube 23, preferably formed of latex. Tube 23 includes an open end sealingly affixed within opening 26 of housing 24. Tube 23 isolates spring 18, wire 22, and the interior of detector unit 14 from water or moisture such that apnea monitor 10 can be completely submerged in water without damage.

Housing 24, preferably formed of sturdy, impact-resistant plastic, includes an aperture exposing a pulsating piezoelectric alarm 100a, a set of light-emitting diodes (LEDs) 102, an event reset button S3, a main ON/OFF switch S1, and downloading memory port 107. As will be described in further detail below, the piezoelectric alarm outputs a high-volume, high-pitch alarm in the event that detector unit 14 detects a period of apnea, or a period of shallow breathing of sufficient length to cause hypoxia. LEDs 102 provide various visual indicators of the status of detector 14, including service unit status, low battery status, moisture or water, penetration status, and apnea event or shallow breathing status. These various status indicators will be described in detail below. Event reset button S3 allows a parent or other caregiver to reset the LEDs. Main switch S1 allows all functions of detector 14 to be activated or deactivated as desired.

As can be seen from FIG. 2b, a bottom surface 106 of housing 24 is curved to fit the curvature of a typical infant. Preferably, the radius of curvature of surface 106 is about six inches. Also illustrated in FIG. 2b is an output terminal 107 provided for memory downloading of data stored within detector 14. Output port 107 includes a pair of output terminals connected to interior terminals I and J, described below. In FIG. 2c, a battery access opening 108 is shown. Access opening 108 allows a parent or other caregiver to replace the main battery of the detector 14 after the low battery detector LED provides an indication that the battery is reaching a state of unacceptably low voltage. Battery access opening 108 preferably includes a rubber O-ring for watertight sealing.

The overall length of belt 12 from ends 16a and 16b is preferably about 20 inches, but may be constructed to other lengths as desired. The overall width of band 12 is preferably about ¾-inch. As will be described more fully below, band 12 is allowed to stretch up to six inches more than its unstretched length of 20 inches. Periodic stretching and relaxation of band 12 provides an indication of normal breathing via relative displacement of wire 22 into and out of detector 14.

Figure 11:
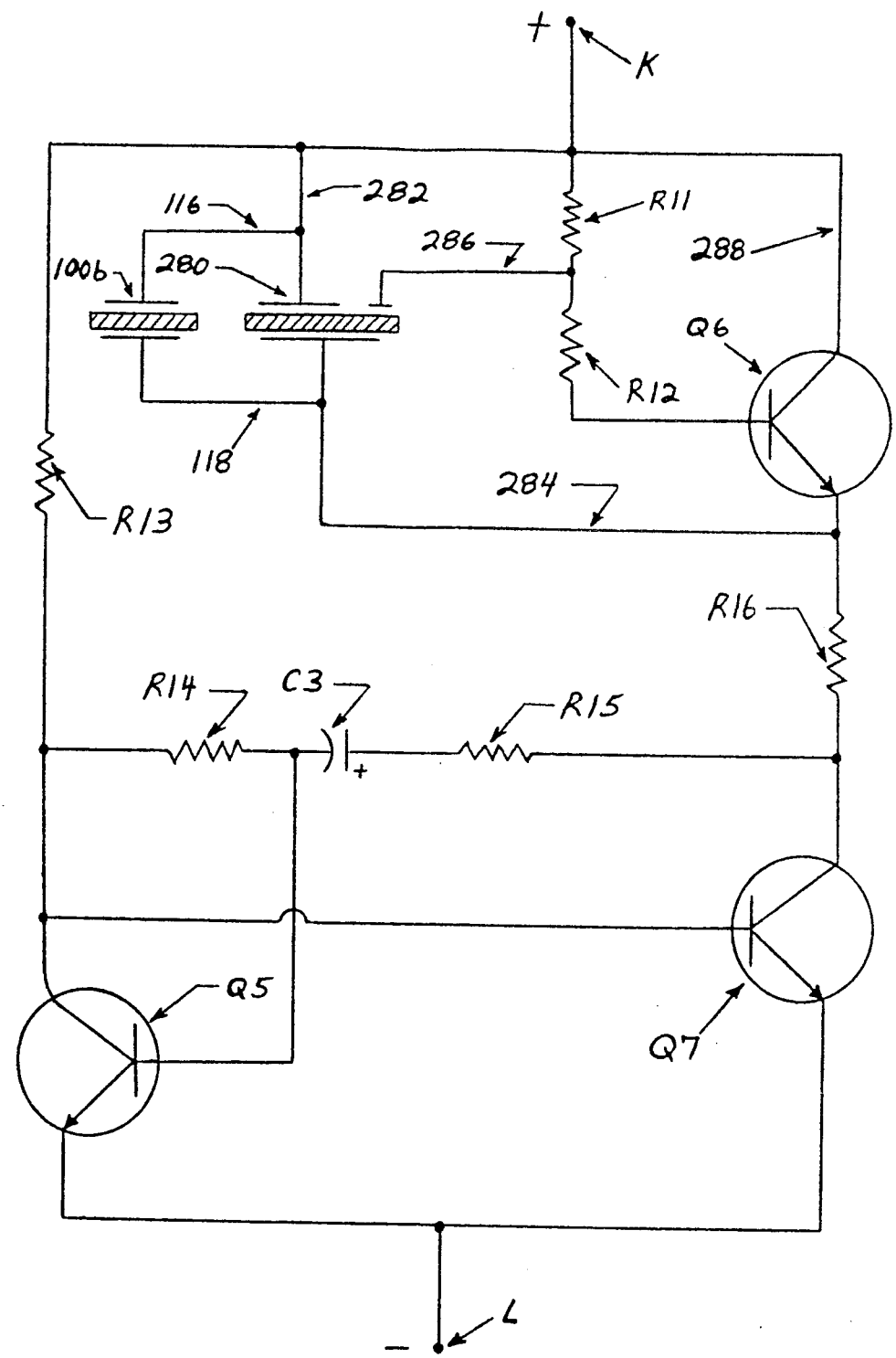
FIG. 11 is a schematic of a subcircuit for the piezoalarm element of FIG. 6.

Pulsating piezoelectric alarm 100b of FIG. 2a is fixedly secured on an outer portion of belt 12, at a distance of approximately six to eight inches as measured from end 16a. Alarms 100a and 100b will always sound simultaneously, thus providing redundancy. Should the orientation of the infant dampen out the sound of either one, the other can still easily be heard. Stretch-limiting wires 116 and 118 will drive alarm 100b, as shown in FIG. 2a and FIG. 11.

Belt 12 comprises two sections which, as described above, each include engaging hook and clasp members to allow mutual attachment. Only the longer portion of belt 12, terminating in end 16b, includes wire 22, spring 18, and latex tube 23 The shorter portion, terminating in end 16a, is merely a portion of elastic fabric attached to housing 24. There is no internal mechanism within the shorter end.

Housing 24 has an overall thickness of about 0.300-inch. Preferably, main switch S1 and event reset switch S3 are recessed within a top portion of housing 24 such that the switches are not easily accidentally switched. Housing 24 may be formed of two plastic portions, sealed together via a waterproof rubber gasket. A seam line connecting the top and bottom portions of housing 24 is shown in FIG. 2b, and identified by reference numeral 109.

Belt 12 is preferably formed of two elastic fabric strips sewn along their longitudinal edges, 12a, FIG. 2b, to provide a single flat, tubular band for enclosing wire 22, spring 18, tube 23, and termination bar 19.

Figure 2F:
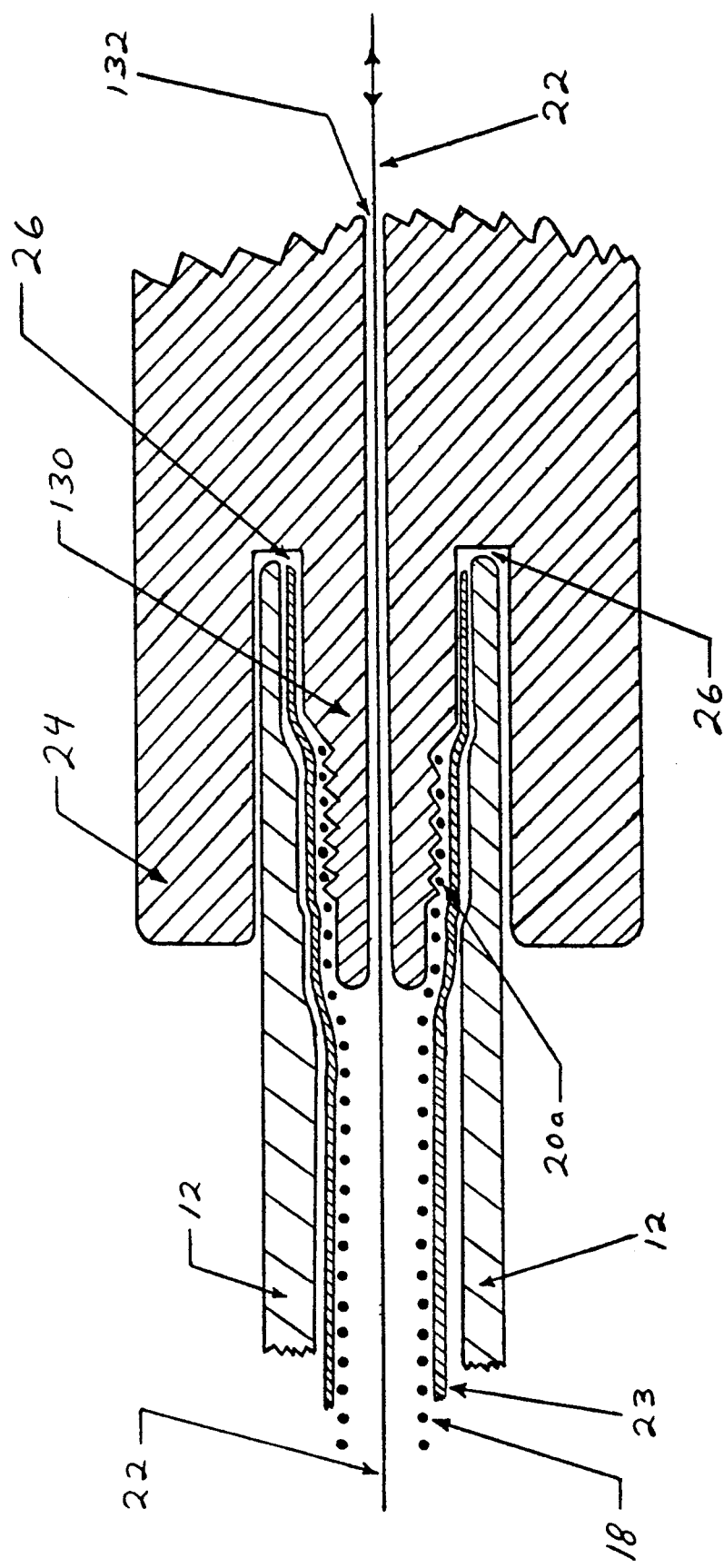

Referring to FIGS. 2d-2f, the internal components of belt 12 are shown in detail, particularly illustrating the mechanism by which these components are attached to belt 12 and to detector unit 14. In FIG. 2d, free end 16b of belt 12 is illustrated. Termination bar 19, preferably formed of solid hard nylon, is a rigid member which extends perpendicularly along end 16b of belt 12. Termination bar 19 is a substantially E-shaped member having a plurality of small bore holes 110 formed along a straight rear portion thereof. Bore holes 110 allow member 19 to be sewn directly into the fabric of belt 12, thus securing member 19 to end 16b of belt 12. Upper and lower protruding tabs 112 and 114, respectively, each include a small bore for allowing a pair of stretch-limiting wires 116 and 118 to be affixed. Opposing ends of stretch-limiting wires 116 and 118 are affixed to detector unit 14 (FIG. 2f). Although not shown, stretch-limiting wires 116 and 118 may be confined within respective channels within belt 12. This is achieved by sewing the top and bottom halves of the belt together on both sides of each wire. All longitudinal sewing on belt 12 is of the expandable stretch-stitch type. By isolating the stretch-limiting wires, interference with spring 12 and wire 22 is avoided. The stretch-limiting wires 116 and 118 thus function both as a feed to piezo-element 100b and prevent overstretching of belt 12.

Stretch-limiting wires 116 and 118 are provided with sufficient slack to allow belt 12 to be expanded or stretched about six inches beyond its unstretched length. However, stretch-limiting wires 116 and 118 prevent the belt from being stretched beyond this amount, thus ensuring that spring 18 is not damaged, and an inner end of wire 22 is not accidentally detached from within detector unit 14. Hence, stretch-limiting wires 116 and 118 provide a safeguard to ensure that belt 12 is not stretched beyond its limits. The amount of slack provided within stretch-limiting wires 116 and 118 is selected prior to manufacturing, in accordance with the displaceability of wire 22 and the stretchability of spring 18. Preferably, stretch-limiting wires 116 and 118 are formed of a thin, durable wire Type 302 stainless steel material having a diameter of about 0.008-inch and an AMS 5688 spring temper.

An outer end 120 of latex tube 23 connects to a cylindrical protruding tab 122 of termination member 19. Although a variety of attachment mechanisms may be employed, preferably tab 122 has a threaded external surface of a diameter somewhat greater than an inner diameter of latex tube 23. In this manner, a terminal portion 124 of spring 18 may be wound onto threads of tab 122, thus securing spring 18 to termination member 19. Furthermore, outer end 120 of latex tube 23 is stretched and pulled over tab 122, thereby affixing tube 23 to termination member 19 Additionally, adhesive may be employed over tab 122 to help affix spring 18 and tube 23 to member 19. Importantly, a watertight connection are provided, hence, water-insoluble adhesives are employed. In this manner, water is prevented from penetrating the interior of tube 23, and thereby possibly penetrating the interior of detector unit 14 and damaging or disabling the electronics mounted therein.

Referring to FIGS. 2e and 2f, the mechanisms by which opposing ends of spring 18, wire 22, tube 23, and stretch-limiting wires 116 and 118 are attached to detector unit 14 will now be described.

A portion of housing 24 includes a pair of projecting tabs 126 and 128. Proximal ends of stretch-limiting wires 116 and 118 are connected, respectively, to tabs 126 and 128. Likewise, housing 24 includes a central protruding cylindrical member 130, similar to middle tab member 122 of member 19, which provides a base for mounting proximal ends of spring 18 and latex tube 23. As before, an external surface of the mounting member is preferably threaded to provide a base for affixing spring 18, with tube 23 stretched over member 130 to provide a watertight seal. However, unlike the distal end of wire 22, which is affixed to termination member 19, a proximal end of wire 22 is not affixed to member 130, but passes into the interior of housing 24, as shown in FIG. 2f. To receive wire 22, cylindrical mounting member 130 includes an internal concentric narrow-diameter bore 132 for closely receiving wire 22 without hindering free movement of the wire.

FIG. 2f also illustrates the manner by which a proximal end of elastic belt 12 is connected to housing 24. As can be seen from FIG. 2f, a pair of slots are formed within housing 24 immediately above and below mounting member 130. Top and bottom portions of elastic band 12 are secured within the slots immediately above and below latex tube 23. A variety of conventional mounting mechanisms may be employed to secure elastic band 12 within the slots. For example, although not shown, proximal ends of elastic band 12 may be sewn into plastic members which are themselves adhesively secured within the slots.

Taking FIGS. 2d-2f together, it can be appreciated that latex tube 23 provides a waterproof conduit for holding spring 12 and wire 22. The elasticity of band 12, in combination with the slack provided in stretch-limiting wires 116 and 118, allow belt 12 to be stretched and retracted in response to breathing. In this manner, a proximal end of wire 22, shown extending into the interior of housing 24 in FIG. 2f, is displaced into and out of the housing with each breath. Latex tube 23, and the manner by which it is affixed at its opposing ends, ensures a watertight seal such that the interior of detector 14 is not penetrated by water or moisture, even if monitor 10 is completely immersed in water.

Figure 4:
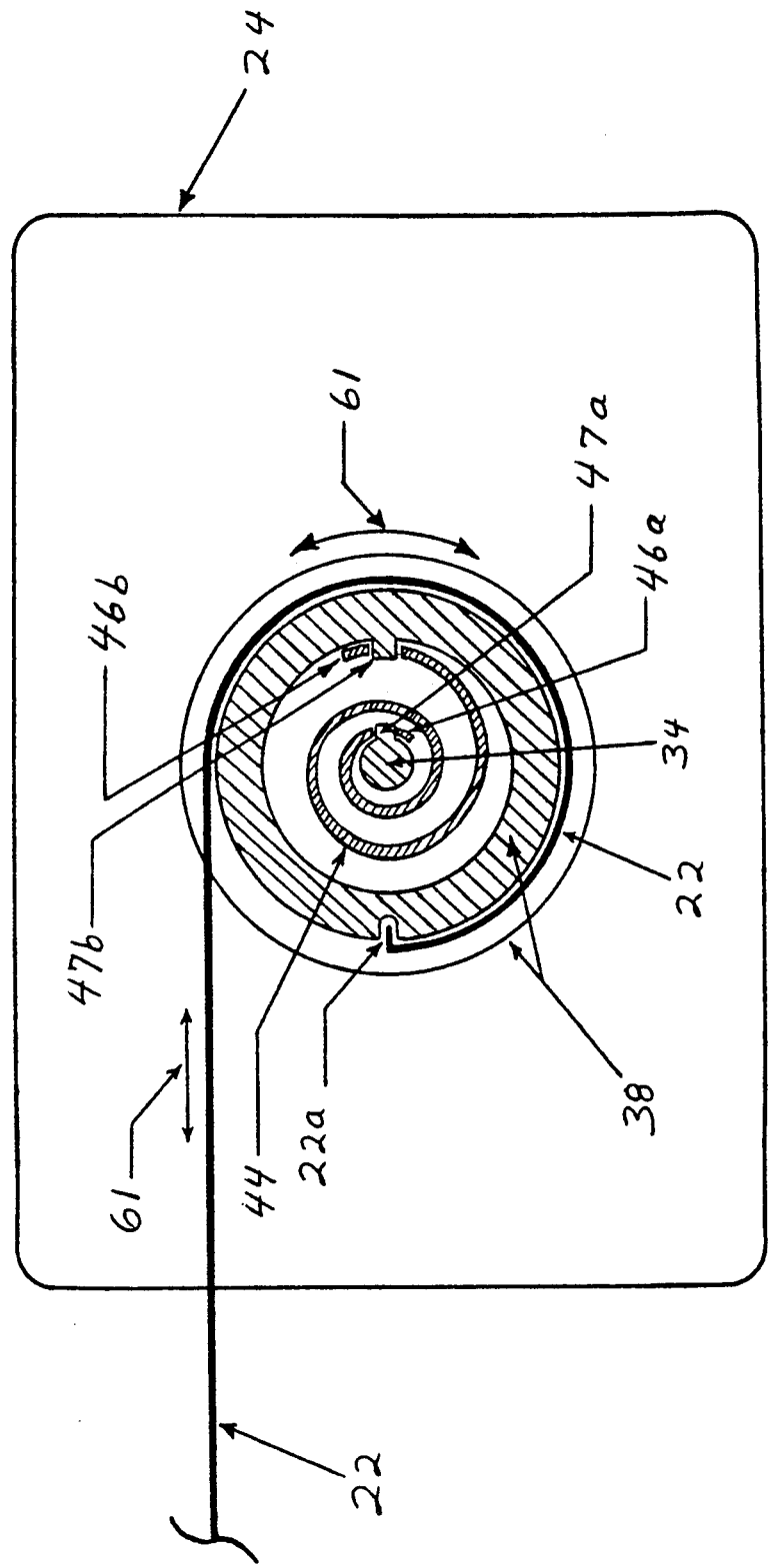
FIG. 4 is a horizontal cross-section of a portion of the detector unit of FIG. 3.

Referring to FIGS. 3 and 4, an interior portion of detector unit 14 is shown in vertical and horizontal cross-sections, respectively. Detector unit 14 includes first and second substantially planar members 30 and 32, which are affixed to an interior surface of housing 24. An axial post 34 extends perpendicularly outward from planar member 32. Planar member 30 includes a bore 36 aligned with the axis of axial post 34.

A barrel 38 is provided between planar members 30 and 32. Barrel 38 includes an axial stem 40 extending into bore 36 of planar member 30. Barrel 38 also includes a cylindrical central chamber 42 in which a coil spring 44 is disposed.

Coil spring 44 includes an inner end 46a and an outer end 46b, with inner end 46a fixedly mounted to axial stem 34 by means of a tab 47a, and outer end 46b is fixedly attached to an interior surface of cylindrical bore 42 by means of tab 47b.

In this configuration, barrel 38 is rotatable along the axis of stem 34 between planar members 30 and 32. The provision of coil spring 44 connecting barrel 38 to axial stem 34 biases the rotation of barrel 38. Coil spring 44 thereby operates as a recoil mechanism.

Barrel 38 includes a concentric circumferential pulley groove 46 provided on an outside surface thereof. A proximal portion of wire 22, received through bore 132 shown in FIG. 2f, is wrapped around circumferential pulley groove 46 with an end 22a of wire 22 fixedly attached to a notch formed along the circumference of barrel 38.

As wire 22 is displaced outwardly from housing 24 by an expansion of belt 12, barrel 38 is caused to rotate, allowing wire 22 to unwind from barrel 38. Simultaneously, coil spring 44 is wound within cylindrical bore 42, thus providing a biasing torque opposing rotation of barrel 38. Then, upon a contraction of belt 12, spring 44 causes barrel 38 to rotate in the opposite direction, thus winding wire 22 around barrel 38 and simultaneously unwinding spring 44. Therefore, barrel 38 returns to a predisplaced configuration with wire 22 wound around circumferential pulley groove 46.

Antifriction coatings are preferably provided along all contact points between barrel 38 and planar members 30 and 32 such that barrel 38 rotates freely and smoothly.

Housing 24 (FIG. 3) is preferably internally lined with a very thin stainless steel foil having a thickness of about 0.0005 inch. This lining provides a static electricity grounding shield for protecting the various field effect devices inside the housing.

Spring 18, sensing wire 22, and stretch-limiting wires 116 and 118 are all preferably formed of Type 302 stainless steel, with an AMS5688 spring temper. Barrel 38 and planar members 30 and 32 are also made of Type 302 stainless steel, and require no particular spring temper, but are preferably stress-relieved.

Figure 5:
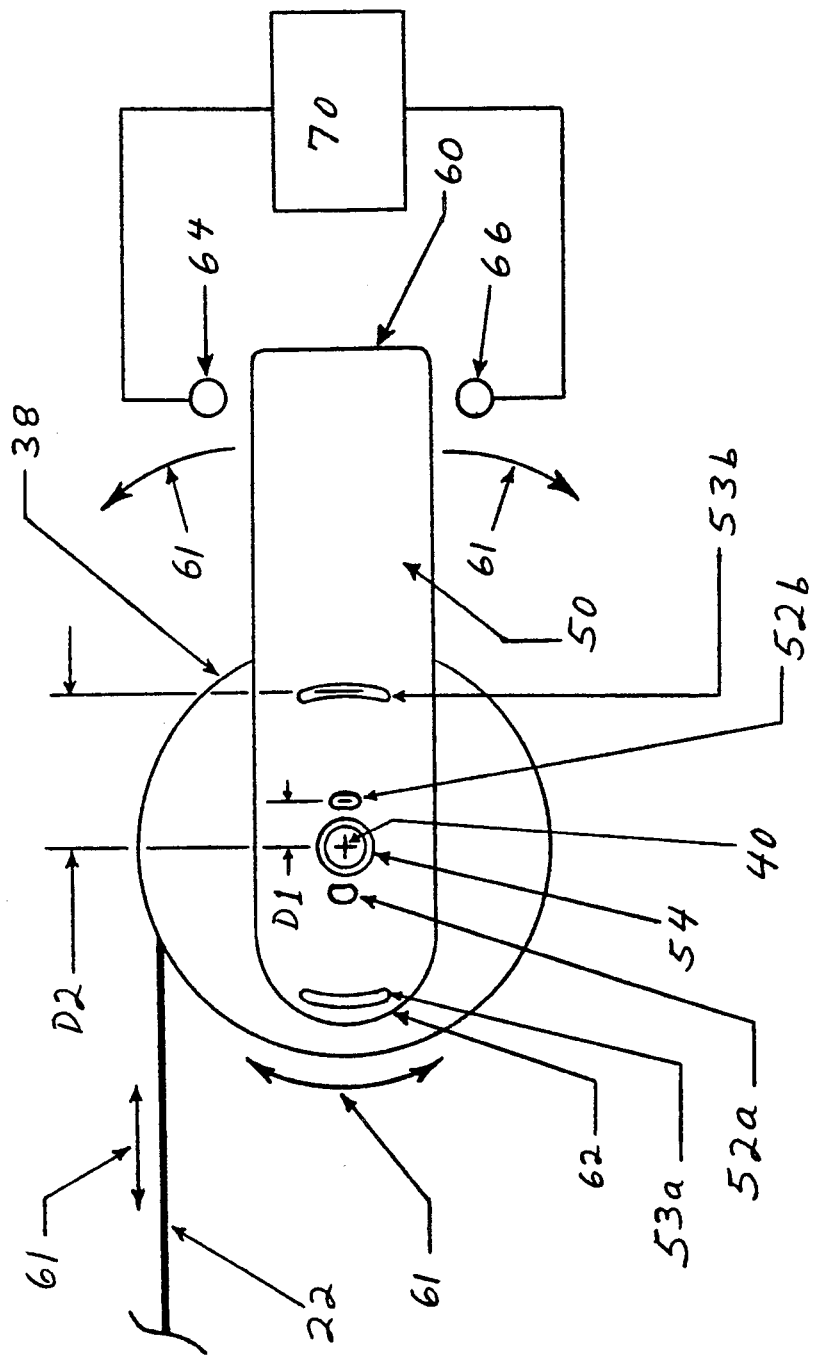
FIG. 5 is a top illustration of the detector unit of FIG. 3.

Referring to FIGS. 3 and 5, a sensing arm 50 is confined between a side surface of barrel 38 and the adjacent side surface of planar member 30. Sensing arm 50 is generally long and narrow and is radially confined about stem 40 of barrel 38 by a central bore 54, as shown in FIG. 5. Sensing arm 50 includes abutting portions 52a and 52b and 53a and 53b. Abutting portions 52a and 52b abut against planar member 30 at a radial distance D1 from the axis of stem 40. Abutment members 53a and 53b abut against a side surface of barrel 38 at a radial distance D2 from the axis of stem 40.

As barrel 38 rotates, sensing arm 50 is likewise caused to rotate by friction between abutment portions 53a and 53b. A corresponding amount of friction occurs along abutting portions 52a and 52b, however, since distance D2 is greater than D1, torque acting on sensing arm 50 is greater at abutment points 53a and 53b than at abutment points 52a and 52b. The greater torque due to distance D2 ensures that sensing arm 50 is carried along with barrel 38, even though an equal amount of friction may occur between sensing arm 50 and planar member 30 and between sensing arm 50 and barrel 38.

Referring to FIG. 5, sensing arm 50 includes ends 60 and 62, with end 60 extending beyond barrel 38, and end 62 extending only slightly greater than D2 beyond the axis of stem 40, but not beyond barrel 38. As sensing arm 50 is rotated along with barrel 38, end 60 sweeps out an arc. Arrows 61 are provided in FIG. 5 showing the direction of motion of wire 22, barrel 38, and sensing arm 50. A fixed member including posts 64 and 66 is provided. Posts 64 and 66 are positioned within the path of sensing arm 50 such that as belt 12 expands or contracts and as barrel 38 rotates in response thereto, sensing arm 50 contacts either post 64 or 66. Further, posts 64 and 66 limit the degree of angular rotation of sensing arm 50 and confine the rotation to a narrow angle.

Posts 64 and 66 thereby serve an important function of confining the degree of rotation of sensing arm 50 despite a possibly large rotational displacement of barrel 38. If belt 12 is stretched considerably while being initially mounted to a patient, wire 22 will unwind from barrel 38, causing barrel 38 to rotate through a large angle. Yet sensing arm 50 will remain between posts 64 and 66, i.e., abutting portions 52a and 52b will slide along barrel 38 as barrel 38 rotates. Thereby, detector unit 14 can detect any small amount of displacement of wire 22 regardless of how much expansion of belt 12 is initially required to snugly fit the patient.

Preferably, a total gap distance available for displacement of sensing arm 50 is 0.015-inch. In other words, with sensing arm 50 abutting post 64, an opposing end of sensing arm 50 is only 0.015-inch from post 66. Sensing arm 50 may have an overall width of about 0.200-inch and an overall length from its pivoting point of about 0.600-inch. Sensing arm 50 is preferably formed from stress-relieved Type 304 stainless steel, gold plated. At its pivot point, sensing arm 50 may have an interior radius of about 0.0333-inch and an exterior radius of about 0.100-inch.

As the infant breathes, sensing arm 50 alternately strikes either post 64 or 66. An electrical circuit 70, discussed below with reference to FIGS. 6 and following, detects contact between sensing arm 50 and posts 64, 66. Circuit 70 includes a timing circuit for measuring time intervals between consecutive contacts between sensing arm 50 and posts 64, 66. Circuit 70 thereby measures time intervals between consecutive respirations of the infant. Circuit 70 includes a determination portion which determines whether the measured time interval has exceeded a predetermined time interval. For example, if the predetermined time interval is set at manufacture to 35 seconds and no respiration occurs for a period of time greater than 35 seconds, an alarm is activated. To this end, circuit 70 is provided with an indication means such as a piezoelectric alarm for providing audible and visual LED indications that the infant has ceased breathing.

Referring to FIGS. 6–10, circuit 70 will now be described in detail. Main circuit 70 includes electrical components for automatically activating piezoelectric alarms 100a and 100b in the event no breathing is sensed for a period of 35 seconds of more. Additionally, main circuit 70 includes a set of subcircuits, described in detail below with reference to the remaining figures, which provide specialized subfunctions. In particular, a rolling memory and shallow breathing indicator circuit 200 is provided for recording an indication of each breath as breathing continues, and for determining periods of shallow breathing. Also included is a low battery circuit 202 for evaluating the voltage of battery B1 and for providing a visual signal via one of the set of LEDs 102 (FIG. 2a) if battery B1 falls below a minimum acceptable voltage. A moisture indicator circuit 204 is provided which provides a visual indication, also via LEDs 102, in the event moisture penetrates the interior of the detector 14, thereby threatening reliable operation of the electronics of circuit 70. Also included is a service unit indicator circuit 206 which provides a visual indication when maintenance servicing of apnea monitor 10 becomes advisable.

To detect periods of apnea, a pair of transistors Q1 and Q2 are connected via their sources to pole 2 of single-pole/double-throw switch S2, which is, in turn, connected to the negative side of battery B1. Single-pole/double-throw switch S2 is a schematic representation of the sensing arm mechanical apparatus described above with reference to FIG. 5 and functions as a micro-mini S.P.D.T. rotary slide switch. A gate of transistor Q2 is connected to terminal 1 of switch S2, and a gate of transistor Q1 is connected to terminal 3 of switch S2. Terminals 1 and 3 of switch S2 correspond to posts 64 and 66 of FIG. 5, and pole 2 corresponds to sensing arm 50. A pair of capacitors C1 and C2 and a pair of resistors R2 and R1 are provided as shown on the gate side of transistors Q2 and Q1. A drain of each transistor Q1 and Q2 is connected directly into terminal L of piezoelectric alarm 100a. Resistors R1 and R2 are connected into terminal K of piezoelectric alarm 100a. With this circuit configuration, a continued switching of switch S2 is required to prevent activation of piezoelectric alarms 100a and 100b. More specifically, as capacitor C1 charges through resistor R1, transistor Q1 activates, thus activating piezoelectric alarms 100a and 100b. Transistor Q1 is a MOSFET and provides an almost infinite input impedance, typically $10^{15}$ ohms. The high impedance of transistor Q1 is highly advantageous, since transistor Q1 thereby has no effect on the charging time of capacitor C1. Rather, capacitor C1 acts as if transistor Q1 is not a portion of the circuit. Nevertheless, transistor Q1 effectively monitors the voltage of capacitor C1.

The RC timing constant for the circuit is preferably set to 35 seconds by setting the resistor R1 to 350 megohms, and the capacitance of capacitor C1 to 0.1 microfarad. With these component values, transistor Q1 remains inactive until capacitor C1 has charged for at least 35 seconds. At this point capacitor C1 has reached about 63% of its full 3-volt potential. Transistor Q2, capacitor C2, and resistor R2 are likewise configured and provided with identical respective component values to provide a second RC circuit, also having a timing constant of about 35 seconds. With this configuration, piezoelectric alarms 100a and 100b are activated either via transistor Q1 or transistor Q2 if either capacitors C1 or C2 are not discharged periodically. In other words, pole 2 of switch S2 must periodically switch back and forth between terminals 1 and 3 to periodically discharge capacitors C1 and C2, thereby preventing activation of piezoelectric alarms 100a and 100b. If pole 2 of switch S2 remains connected to terminal 1 (indicating that sensing arm 50 of FIG. 5 is motionless and in contact with post 64), the alarm sounds. Thus, continued breathing is required to stretch belt 12, thereby displacing wire 22 and causing sensing arm 50 to periodically discharge capacitors C1 and C2.

Also included in main circuit 70 is an event indicator 208 having a pair of alternately flashing LEDs 210. Event indicator 208 is connected between pole 2 of switch S2 and SCR1. A gate of SCR1 is connected into the collector of a third transistor Q3, preferably of the bipolar PNP type. A base of transistor Q3 connects via resistor R4 to terminal L of piezoelectric alarm 100a. An emitter of transistor Q3 connects via resistor R3 to terminal K of piezoelectric alarm 100a. Resistor R3 is also connected into the anode of SCR1 via event reset switch S3 (also shown in FIGS. 2a and 6).

With this additional circuitry, LEDs 210 of event indicator 208 are activated whenever piezoelectric alarm 100a is activated. However, whereas piezoelectric alarms 100a and 100b are deactivated once breathing continues, LEDs 210 of event indicator 208 remain flashing. Hence, a visible indication of an apnea event continues, even once the event has terminated. In other words, even though the patient may resume breathing, thereby silencing the piezoelectric alarms 100a and 100b, event indicator 208 remains flashing, thus providing the parent or caregiver with an indication that an apnea event has occurred. This is a particularly desirable feature, since the mere activation of the alarm may be sufficient to induce the breathing of the patient without necessarily summoning the parent or caregiver. In such a circumstance, event indicator 208 provides a visual indication that an event has occurred. To deactivate event indicator 208, the parent or caregiver triggers switch S3, thereby momentarily opening the anode of SCR1, thus resetting event indicator 208.

Preferably, resistor R4 is provided with a 15-megohm resistance, whereas resistor R3 is provided with a 10-kilohm resistance. Transistor Q3 may be a 2N3906PNP-type transistor, or equivalent. MOSFET transistors Q1 and Q2 are preferably N-channel TMOSFET transistors of the BS170 type, or equivalent. SCR1 is a low-power/small signal of the type C203Y GE, or equivalent. Resistors R3 and R4 may be 50-milliwatt metal oxide, SMT resistors or diffused silicon resistors. Resistors R1 and R2 may be 50-microwatt metal oxide surface mount resistors or diffused MOSFET resistors. Capacitors C1 and C2 are preferably monolithic dip capacitors having 25-volt maximums. Switch S1 is preferably a micro-mini linear slide switch having a single-pole/single-throw with a 50-volt DC, 100-milliamp maximum. Preferably switch S1 is within a waterproof enclosure. Switch S2 is preferably a micro-mini rotary slide switch having a single-pole/double-throw with a 30-volt DC and 100-milliamp maximum. Switch S3 is preferably a micro-mini pushbutton single-pole/single-throw switch, normally on, with a 30-volt DC, 50-milliamp maximum. This switch is also preferably waterproof. Battery 1 is preferably a 3-volt lithium cell battery having a 190-milliamp-hour capacity, such as an Eveready ® Part No. CR2032 battery, or equivalent.

Figure 6:
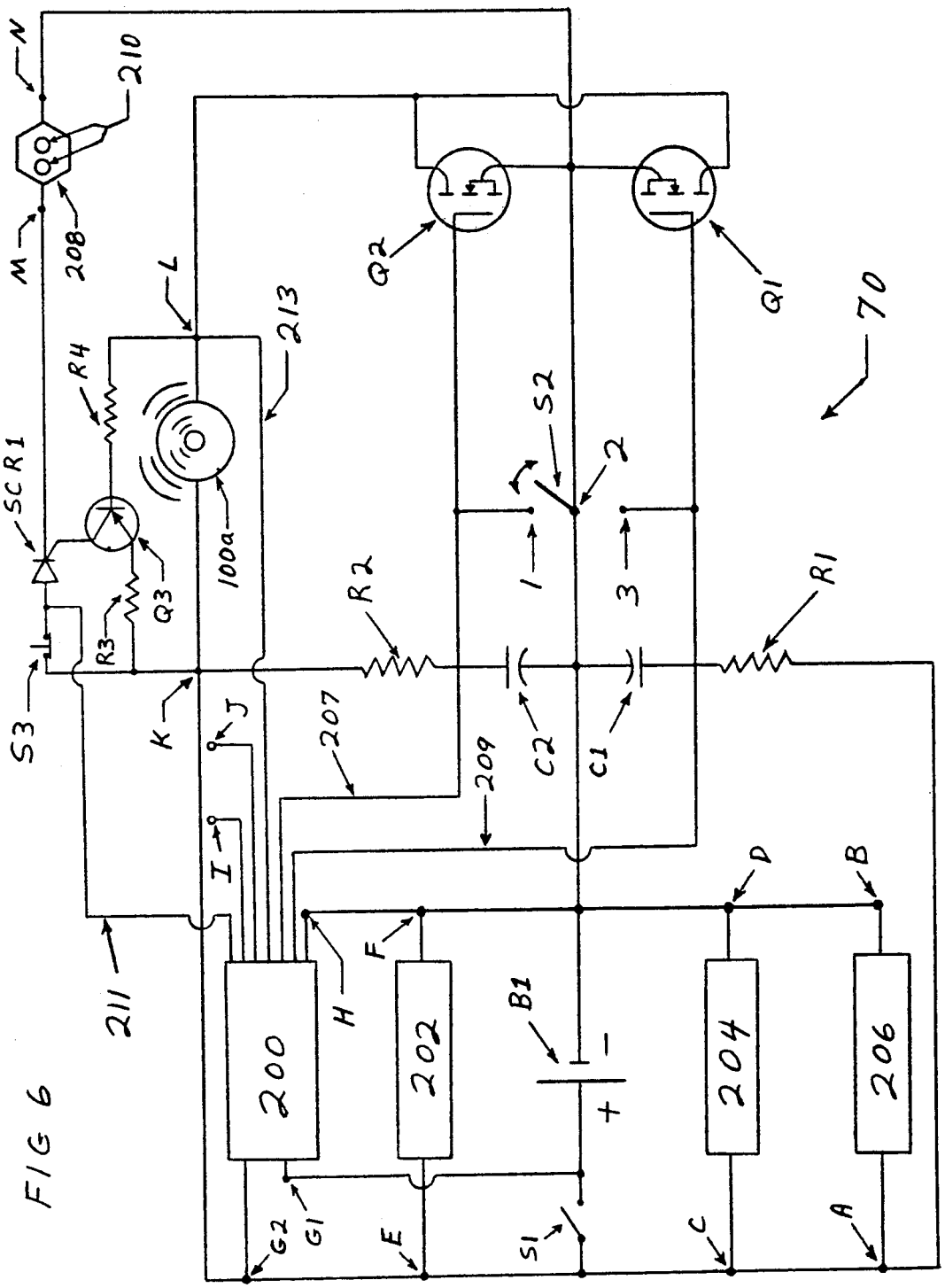
FIG. 6 is a schematic of an electrical circuit of the detector unit of the invention.
Figure 7:
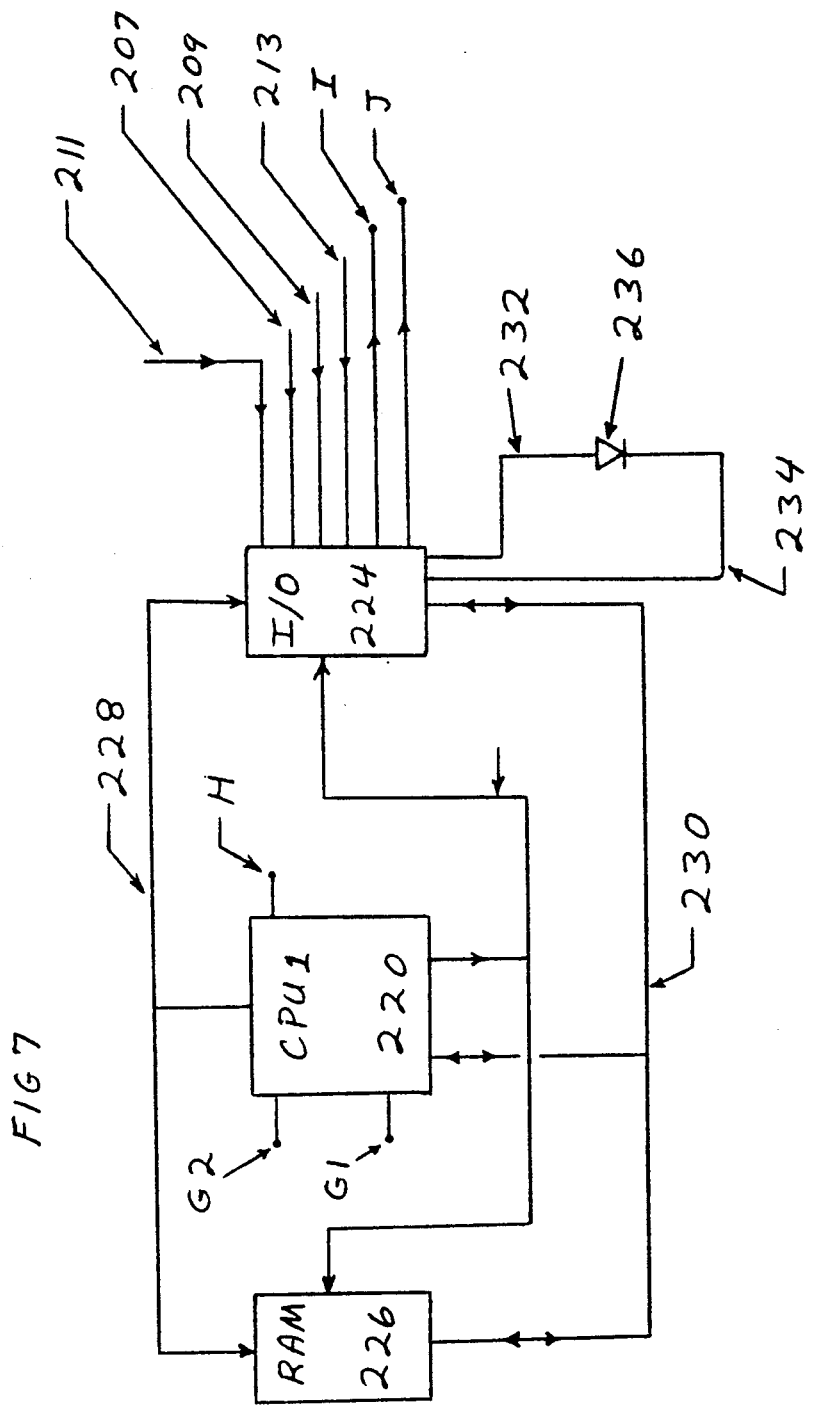
FIG. 7 is a schematic of a subcircuit for the rolling memory and shallow breathing indicator of FIG. 6.

Referring to FIG. 7, a subcircuit for the rolling memory and shallow breathing indicator 200 is illustrated schematically. Subcircuit 200 includes a main CPU 220 with a substantial amount of ROM connected via a control bus 222 to an input/output unit 224 and a rolling memory CMOS static RAM 226. An address bus 228 also connects CPU 220 to input/output unit 224 and rolling memory CMOS static RAM 226. Additionally, a data bus 230 connects CPU 220, input/output unit 224, and rolling memory CMOS static RAM 226. Data bus 230 provides for two-way data transmission between CPU 220 and the input/output unit and the rolling memory CMOS static RAM 226. Address bus 228 and control bus 222 only provide for output from CPU 220. Input/output unit 224 includes two output terminals I and J, shown also in FIGS. 2b and 6, which provide output terminals for downloading data from rolling memory CMOS static RAM 226 to an external data display unit (not shown). Input/output unit 224 includes three additional terminals connected to lines 207, 209, and 211 (FIG. 6). As can be seen from FIGS. 6 and 7, line 207 connects input/output unit 224 to terminal 1 of switch S2 and to the gate of transistor Q2. Line 209 connects input/output unit 224 to terminal 3 of switch S2 and to the gate of transistor Q1. Line 211 connects input/output unit 224 to the low side of switch S3 Line 211 provides a reset line for resetting shallow breathing indicator LED 236. Input/output unit 224 additionally includes lines 232 and 234 leading to an LED 236, which provides a visual indication of shallow breathing.

CPU 220 includes output terminals G1, G2, and H. Terminal H is merely a ground. Terminal G1 connects to battery B1 (FIG. 6) to provide continuous standby power to CPU 1 and to rolling memory CMOS static RAM 226 to maintain the memory even when switch S1 is off. Terminal G2 connects to switch S1 for turning off CPU 220 when switch S1 is turned off.

Input/output unit 224 additionally includes an output line 213 connected to piezoelectric alarm 100a (FIG. 6). This line drops low to activate the piezoelectric alarm.

Broadly, rolling memory and shallow breathing indicator 200 receives signals from switch S2 (FIG. 6) with each breath of the patient. As each signal is received, the signals are stored in binary form in rolling memory CMOS static RAM 226, thus providing a continuous record of respiration signals as a function of time. Thus, if an apnea event occurs, one can download a record of the patient's breathing data both prior to and immediately after the apnea event or episode of shallow breathing.

Additionally, the ROM in CPU 200 may be preprogrammed with algorithms for detecting shallow breathing and activating an alarm when shallow breathing is detected. Generally, shallow breathing occurs when an individual's pauses between successive breaths are too frequent and too long in duration to allow for adequate oxygenation of the blood, thus leading to hypoxia. Hence, by determining the number of breaths during a given period of time, for example, 10 minutes, algorithms preprogrammed in the ROM of CPU 220 are capable of determining when shallow breathing has occurred and when the patient is at risk from hypoxia, which can, in turn, lead to apnea, permanent brain damage, and death.

The near infinite input impedance of the input/output unit 224 "looks" at the action of switch S2 (FIG. 6). If breathing patterns of the patient are indicative of shallow breathing, as determined by preprogrammed algorithms of CPU 200, then LED 236 and piezoelectric alarms 100a and 100b (FIG. 6) are both activated. Algorithms for determining the onset of hypoxia from shallow breathing are conventional and will not be described further.

Preferably, CPU 220 is a TMS9900 or Intel 8085 microcontroller. Rolling memory CMOS static RAM 226 and input/output unit 224 may be any conventional units which are compatible with the particular CPU unit selected for 220. LED 236 is preferably a blinking LED, having a yellow color, such as Archer No. 276-021, 276-055, or equivalent. Other microcomputer chips suitable for use as the rolling memory, the CPU, or the input/output unit include Motorola 6805, CMOS MC146805F2, Siemen's 80C517A, or Intel 8096.

Figure 8:
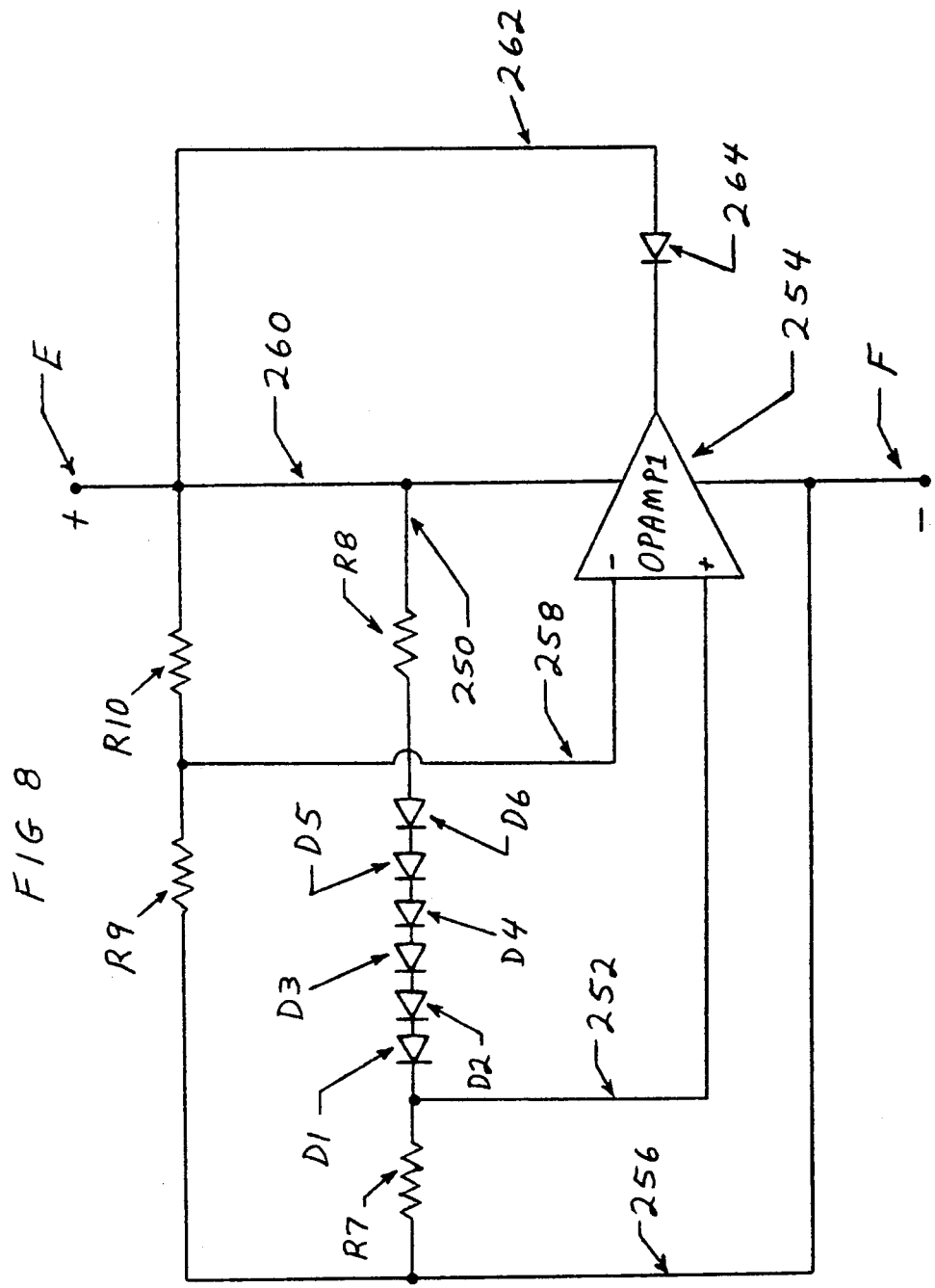
FIG. 8 is a schematic of a subcircuit for the low battery indicator of FIG. 6.

Referring now to FIG. 8, a subcircuit for low battery indicator 202 of FIG. 6 will be described. Subcircuit 202 provides electrical components necessary for determining whether battery B1 (FIG. 6) has dropped below an acceptable voltage. This determination is made before battery B1 drops so low in voltage that it cannot produce a visual signal noting the same, or so low that it cannot still drive the main circuit 70. Subcircuit 202 includes a set of six diodes, D1, D2, D3, D4, D5, and D6, arranged sequentially between a pair of resistors R7 and R8 along path 250. A second path 252 connects line 250 between diode D1 and resistor R7 to the noninverting/terminal of an op-amp 254. A third path 256 connects path 250 at an opposing terminal of resistor R7 to op-amp 254 and to terminal F (FIG. 6). Path 256 additionally connects resistor R7 to a resistor R9. Resistor R9 is, in turn, connected via a path 258 to the inverting terminal of op-amp 254. A resistor R10 connects resistor R9 to terminal E (FIG. 6) via a path 260, which also connects into op-amp 254. Finally, a path 262 connects line 260 via an LED 264 to output of op-amp 254.

With this configuration and with suitable resistance values for resistors R7, R8, R9, and R10, LED 264 is illuminated when battery B1 (FIG. 6) falls below a preselected minimum acceptable voltage level.

More specifically, when the voltage of battery B1 (FIG. 6) is above 2.3 volts, the noninverting input of op-amp 254 is high, whereby LED 264 remains off. However, once the voltage of battery B1 (FIG. 6) falls below 2.1 volts, then the inverting input of op-amp 254 becomes higher than the noninverting input, such that the output of op-amp 254 swings low, thereby illuminating LED 264. This nonlinear response is the result of a threshold voltage that each of the diodes must satisfy to conduct. Thus, the diodes are active elements in the circuit. Resistance values for resistors R7, R8, R9, and R10 must be tuned to provide a proper evaluation of the voltage of battery B1 (FIG. 6). In particular, the following resistance values are acceptable: R7 = 50.83 megohms, R8 = 51.24 megohms, R9 = 6.36 megohms, and R10 = 10.43 megohms. Preferably, each of these resistors is a diffused MOSFET, metal oxide, or SMT 50-microwatt resistor having a variance of not more than ±0.1%. Diodes D1-D6 are each preferably a 1N914 small signal/fast switching diode. Op-amp 254 may be a TLC25L2CP LinCMOS dual low power operational amplifier available from Texas Instruments, or an equivalent. LED 264 is preferably a high-efficiency microsized, red-blinking LED drawing 0.5 milliamps, such as an Archer No. 276-057 or 276-036, or equivalent. The resistance values may be varied accordingly to provide a low battery indication for a voltage other than 2.1 volts.

While the circuit is in an LED OFF state, the total current draw of the circuit is merely 7.8 microamperes. With such a low current draw, the low battery detector circuit can remain continuously on line without significantly draining battery B1. Once LED 264 is illuminated, the operator should replace battery B1 of the unit.

Figure 9:
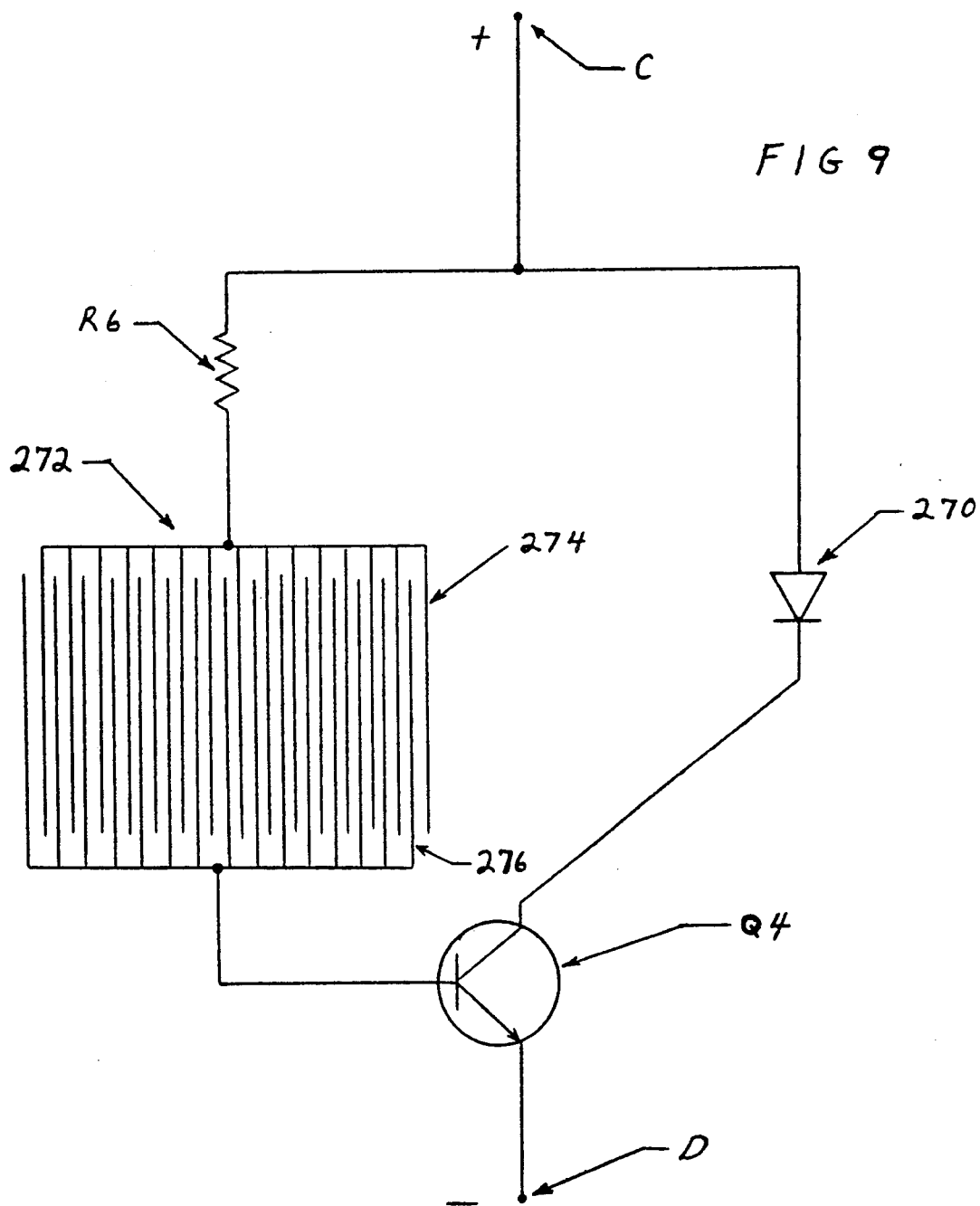
FIG. 9 is a schematic of a subcircuit for the moisture indicator of FIG. 6.

Referring to FIG. 9, a subcircuit for moisture indicator 204 of FIG. 6 is represented schematically. Moisture indicator 204 connects between terminals C and D of FIG. 6 and includes a resistor R6, an LED 270, and a transistor Q4. LED 270 is connected between the collector of transistor Q4 and terminal C. The emitter of transistor Q4 connects to terminal D. Between resistor R6 and the base of transistor Q4 is a moisture grid 272. Moisture grid 272 is a gold-plated copper grid chemically etched onto an interior of housing 24 (FIG. 2a). Soldered tabs (not shown in this schematic) are provided for connecting moisture grid 272 into the remaining components of the moisture indicator circuit. As can be seen from FIG. 9, moisture grid 272 is comprised of a set of generally parallel opposing terminals 274 and 276, with terminals 274 connected via resistor R6 to terminal C, and terminal 276 connected via transistor Q4 to terminal D.

A layer of salt, equivalent to about 90-100 grains of salt (sodium chloride), is uniformly dried onto the surface of moisture grid 272, thereby covering terminals 274 and 276. With the salt layer, should moisture or water enter the interior of detector unit 14, electricity is conducted via moisture grid 272, thereby activating transistor Q4 and illuminating LED 270. In other words, penetration of moisture or water to the moisture grid 272 causes the dried salt thereon to become a salt water electrolyte, thereby allowing for conduction of electricity between opposing terminals 274 and 276. In this manner, LED 270 is activated when water penetrates the interior of detector unit 14, such that the parent or caregiver is alerted to possible moisture damage to the electrical components of detector 14 which may affect the proper operation of the equipment.

Resistor R6 is preferably a 220-kilohm ±5% metal film, diffused or SMT resistor having a 10-milliwatt maximum. Transistor Q4 may be a 2N222 NPN transistor, or an equivalent. LED 270 is preferably a high-efficiency microsized green LED providing either a continuous or blinking illumination, with a minimum voltage of 2 volts and a minimum current of 0.4 milliamperes. LED 270 may, for example, be an Archer No. 276-030 or equivalent.

Figure 10:
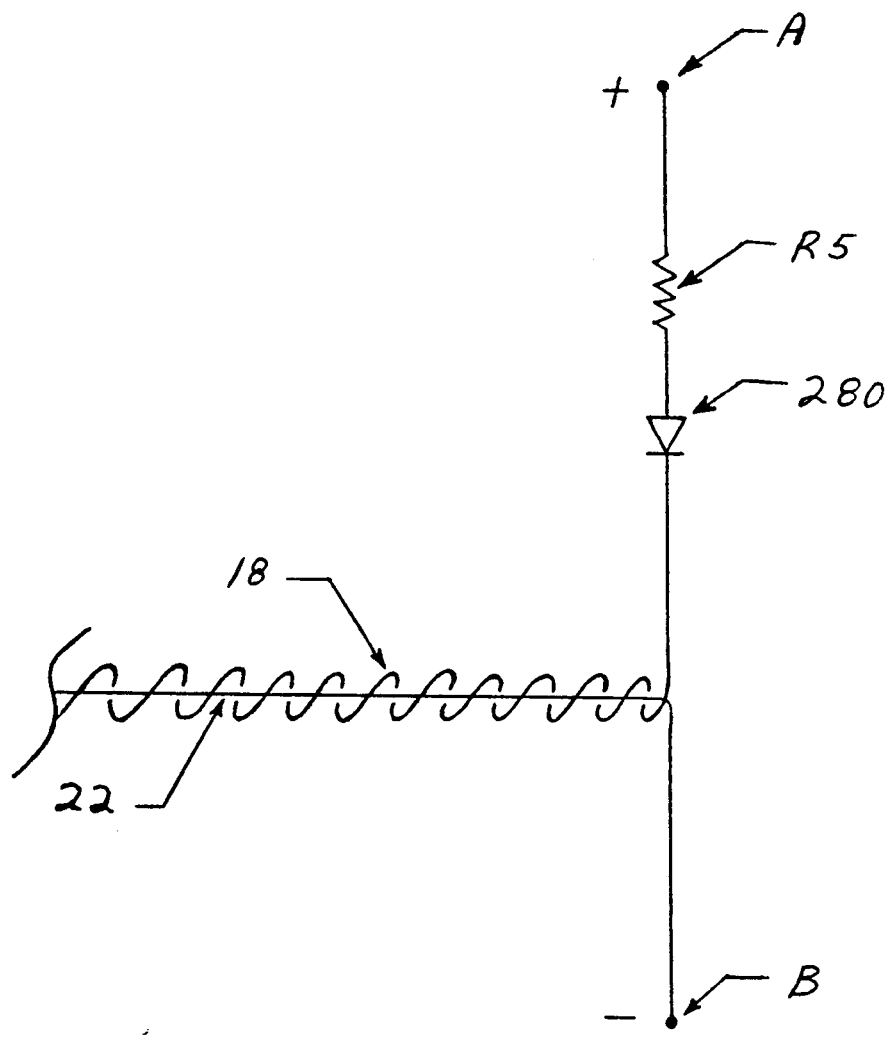
FIG. 10 is a schematic of a subcircuit for the "service unit" indicator of FIG. 6.

FIG. 10 provides a schematic illustration of a subcircuit for service unit indicator 206 of FIG. 6. The service unit indicator provides an indication of possible wear of the Teflon TM -coated sensing wire 22, or the Teflon TM -coated spring 18, of FIG. 2a. Thus, if the Teflon TM coating is worn from wire 22 and spring 18 such that smooth sliding of wire 22 is hindered by friction, service indicator 206 provides a visual signal of the possible wear to the user. To this end, service indicator circuit 206 is provided with a resistor R5 and an LED 280, which connects terminal A (FIG. 6) to spring 18 (FIG. 2a). Terminal B (FIG. 6) is connected into sensing wire 22. In other words, proximal ends of wire 22 and spring 18 are connected into the electronics of detector unit 14. There is no electrical connection of wire 22 and spring 18 at the distal end of these mechanical components on termination bar 19. With this configuration, electrical current passes between terminals A and B only if the Teflon TM coatings on both the sensing wire 22 and spring 18 are worn off to complete the circuit. Thus, if the Teflon TM becomes sufficiently worn, the circuit between terminals A and B is completed, thereby activating LED 280 and providing a visual indication of mechanical wear. As noted above, once Teflon TM is worn from sensing wire 22 and spring 18, these components may not slide smoothly against each other, thereby leading to false or inaccurate apnea or shallow breathing indications. Once LED 280 is illuminated, the parent or caregiver is thereby alerted to have the entire apnea monitor unit 10 serviced or replaced.

Preferably, resistor R5 is a metal film, SMT or diffused resistor having a 50-milliwatt maximum with a resistance of 2 kilohms ±5%. LED 280 may be any of a variety of high-efficiency microsized yellow, non-blinking LEDs with a 2-volt minimum and a 1-milliampere minimum. A suitable LED is the Archer No. 276-005, or equivalents.

Referring to FIG. 11, a subcircuit for the pulsing piezoelectric alarms 100a and 100b (FIG. 6) is represented schematically. Piezoelectric alarm circuit 100a connects between terminals K and L (FIG. 6), and includes three transistors, Q5, Q6, and Q7, connected in combination with resistors R11-R15 and capacitor C3. Also included is a piezocrystal element 280 having an input line 282, an output line 284, and a feedback line 286. In accordance with conventional piezocrystal nomenclature, input line 282 is red, output line 284 is black, and feedback line 286 is blue. Line 284 connects piezocrystal element 280 to the emitter of transistor Q6, whereas feedback line 286 connects via resistor R12 to the base of transistor Q6. A path 288 directly connects terminal K into the collector of transistor Q6. With an application of voltage across piezocrystal 280, the crystal charges, thereby deforming in one direction. As the piezocrystal snaps back to its original shape, it creates a negative electrical pulse along feedback line 286, thus turning off transistor Q6. When crystal 280 again reaches an equilibrium state, the just-described cycle repeats, creating an audible tone at about 2900 Hz.

Transistors Q5 and Q7 turn each other on and off in a self-starting free-running fashion. This on/off sequence, in turn, causes on/off cycling of the piezocrystal 280 at a cycle rate determined by the resistances of resistors R4 and R15 and the capacitance of capacitor C3. Preferably, resistor R14 has a resistance of 10 kilohms, whereas resistor R15 has a resistance of 33 kilohms. Capacitor C3 has a capacitance of 1 microfarad with 25 volts. With these components, the pulsing frequency of piezocrystal element 280 and, hence, piezoelement 100b is about 4 Hz.

Resistors R13 and R16 are current-limiting resistors having resistances of 15 kilohms and 1 kilohm, respectively. Resistor R11 preferably has a resistance of 220 kilohms, whereas resistor R12 has a resistance of 10 kilohms. Transistors Q5, Q6, and Q7 are preferably MPS2222A or equivalent NPN-type small signal transistors. All resistors shown in the schematic of FIG. 11 are preferably metal film or SMT resistors ±1%, ⅛-watt maximum. Preferably, capacitor C3 is an electrolytic or tantalum capacitor. A second piezocrystal element 100b is mounted on belt 12, and connected via stretch-limited wires 116 and 118 as shown in FIG. 2b, to lines 282 and 284, thus connecting piezocrystal element 100b in parallel with piezocrystal element 280.

With a 50% duty cycle, the current draw of the piezocircuit of FIG. 11 is about 0.8 milliampere, yet produces a loudness of about 85 decibels ±5%. At 85 decibels, the piezoalarm is sufficiently loud to alert a parent or other caregiver in the vicinity of the patient that an apnea event or shallow breathing has occurred, even if the infant has rolled over on top of piezoalarm 100b, the other alarm will be heard, since it is displaced six to eight inches from piezoalarm 100a (see FIG. 2a). In some cases, the volume is likely to be sufficient to revive the patient, thereby directly causing breathing to resume. The event indicator however, will still be activated.

Figure 12:
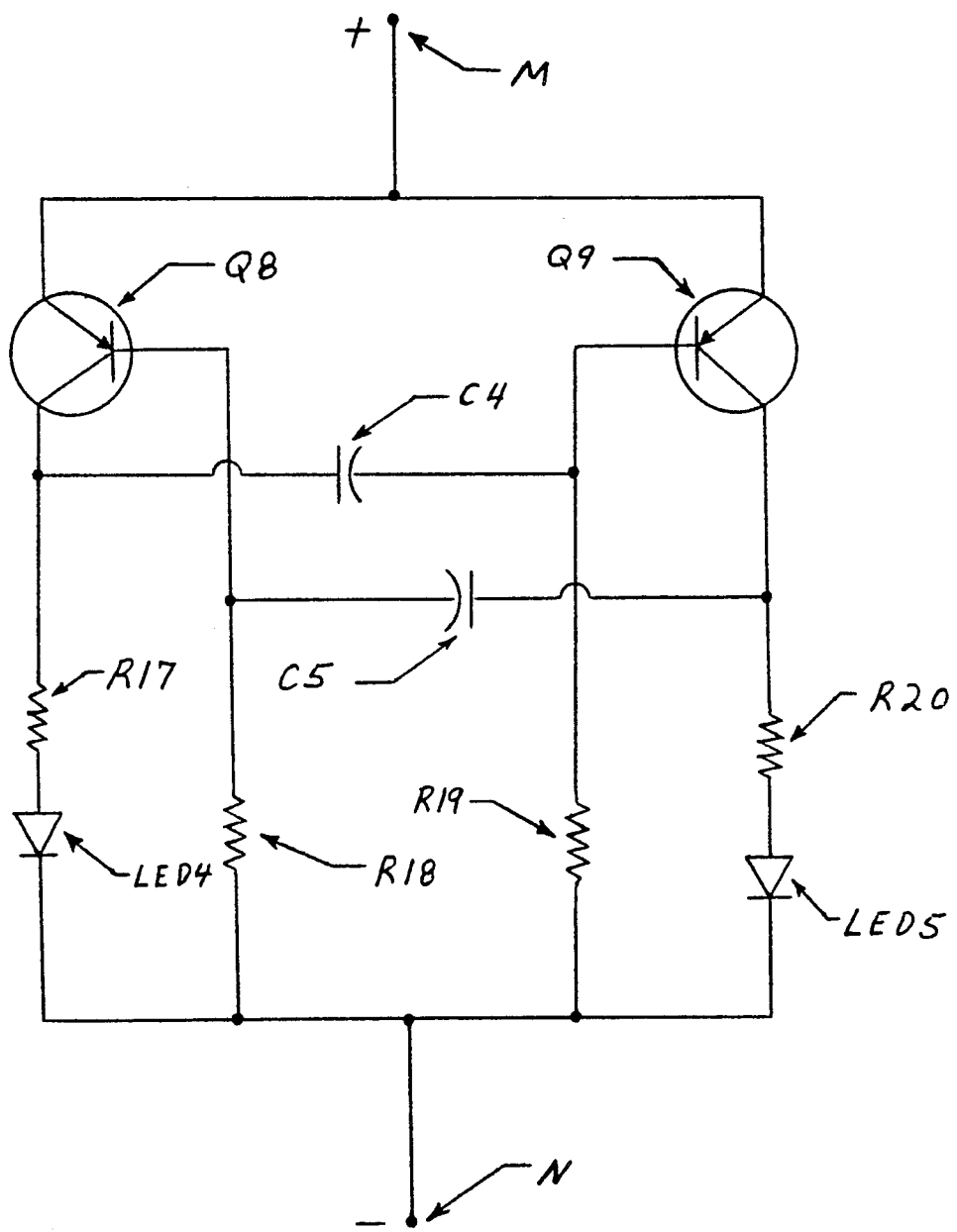
FIG. 12 is a schematic of a subcircuit for the "event indicator" of FIG. 6.

Referring to FIG. 12, a subcircuit for event indicator 208 (FIG. 6) is represented schematically. Event indicator circuit 208 includes a pair of transistors Q8 and Q9, each having a pair of collectors connected via resistors to a pair of LEDs. Paired more specifically, the collector of transistor Q9 is connected via resistor R20 to LED 5, whereas the collector of transistor Q8 is connected via resistor R17 to LED 4. The bases of transistors Q8 and Q9 are respectively connected via resistors R18 and R19 to opposing terminals of LED 4 and LED 5 and directly to terminal N. Positive terminal M is connected into the emitters of transistors Q8 and Q9. Capacitors C4 and C5 are provided, as shown, for producing a multivibrator circuit which acts to alternately activate LED 4 and LED 5. More specifically, transistors Q8 and Q9 turn each other on and off at a rate determined by the resistance values of resistors R18 and R19 and the capacitance of capacitors C4 and C5. These components together provide a free-running multivibrator mode. Resistors R17 and R2 operate to limit the current to the respective LEDs, which flash alternately.

Preferably, resistors R18 and R19 are 1-megohm ±1%, 100-microwatt resistors, of either metal oxide, SMT, or diffused MOSFET configuration. Capacitors C4 and C5 are preferably 1-microfarad, 10-volt electrolytic or tantalum capacitors. Resistors R17 and R20 are preferably 1-kilohm ±1%, 50-milliwatt resistors of metal film, SMT, or diffused configurations. With these component values, a pulse rate of LED 4 and LED 5 of 3 Hz is achieved. With a duty cycle for each LED of 50% and an overall duty cycle of 100%, the total current draw at 3 volts DC for the event indicator circuit is 0.38 milliampere. Transistors Q8 and Q9 are preferably 2N3906 PNP-type transistors, or equivalent.

Thus, the event indicator subcircuit 208 of FIG. 12 operates to alternatingly activate a pair of LEDs to provide a clear visual indication of an apnea event or shallow breathing. As noted above, event indicator 208 remains flashing even after the event or period of shallow breathing has passed, whereas the piezoelectric alarm is deactivated once the event or period of shallow breathing has passed. The flashing of the LEDs of event indicator 208 is only terminated either by opening switch S3 or by deactivating the entire detector circuit via switch S1 (FIG. 6). However, it is recommended that switch S3 be used to reset event indicator 208.

What has been described thus far is an apnea monitor having a mechanical breath sensor, S2, utilizing a metal sensing arm which swings back and forth between a pair of electrical terminals connected into a sensing circuit. In the embodiment shown in FIG. 13, the mechanical sensing arm is replaced with a magnetic induction sensing device. The magnetic induction sensor, in addition to providing an indication of each breath, provides volumetric breathing information for providing a more accurate and reliable detection of shallow breathing. An apnea monitor constructed in accordance with the alternative embodiment using a magnetic induction sensing coil is substantially identical to that of the mechanical embodiment described above. Only differences between the embodiments will be described herein.

Figure 13:
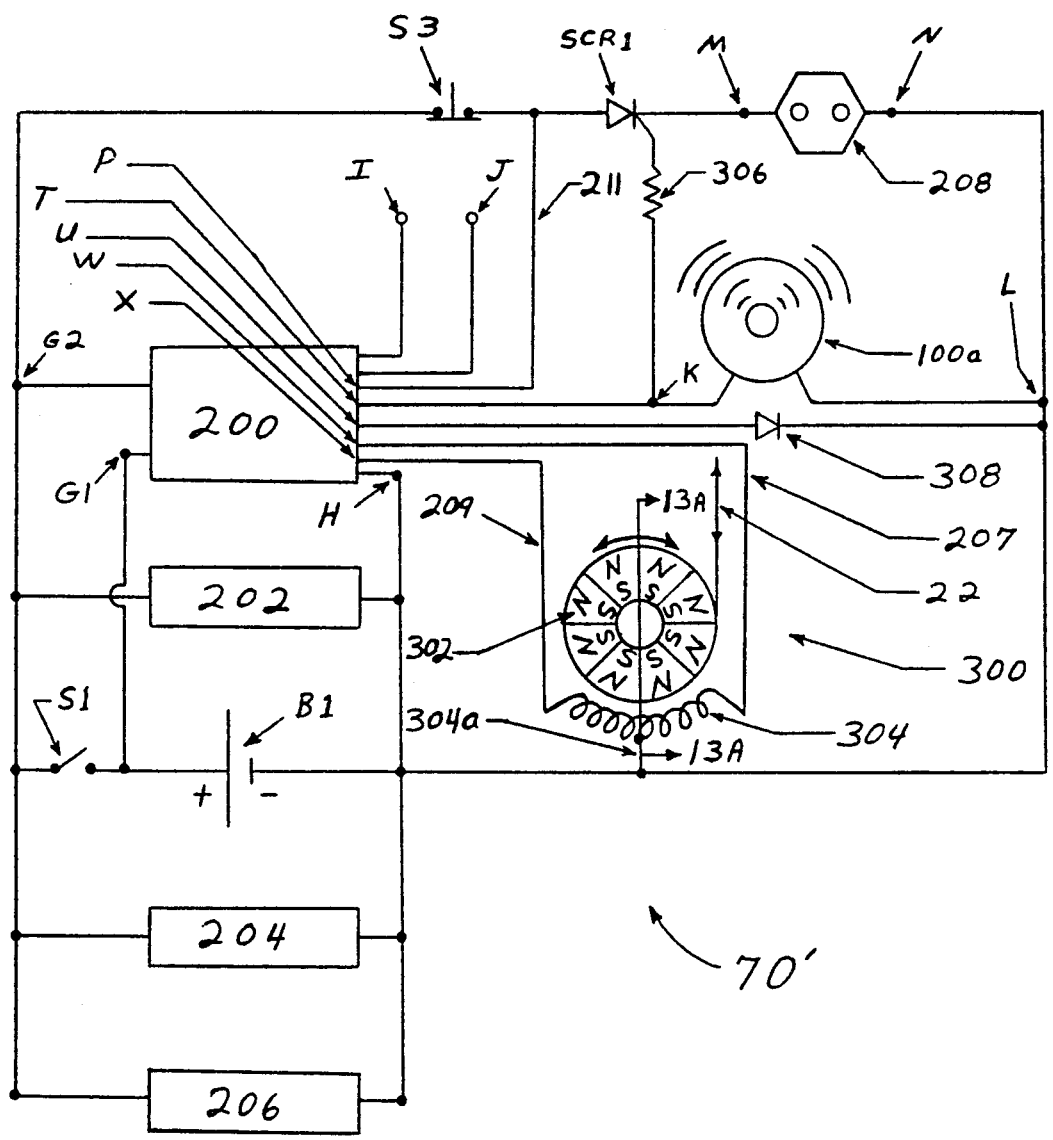
FIG. 13 is a schematic of an alternative embodiment of the circuit of FIG. 6.

Referring to FIG. 13, a main circuit for a magnetic induction embodiment is represented schematically. Circuit 70' of the magnetic induction embodiment is similar to circuit 70 of FIG. 6 of the mechanical embodiment, but includes a magnetic induction sensor 300 in place of transistors Q1 and Q2, resistors R1 and R2, and capacitors C1 and C2, and mechanical single-pole/double-throw switch S2. Magnetic induction sensor 300 is connected into rolling memory and shallow breathing indicator 200 directly via paths 207 and 209 feeding into terminals W and X of the shallow breathing indicator 200.

Figure 13A:
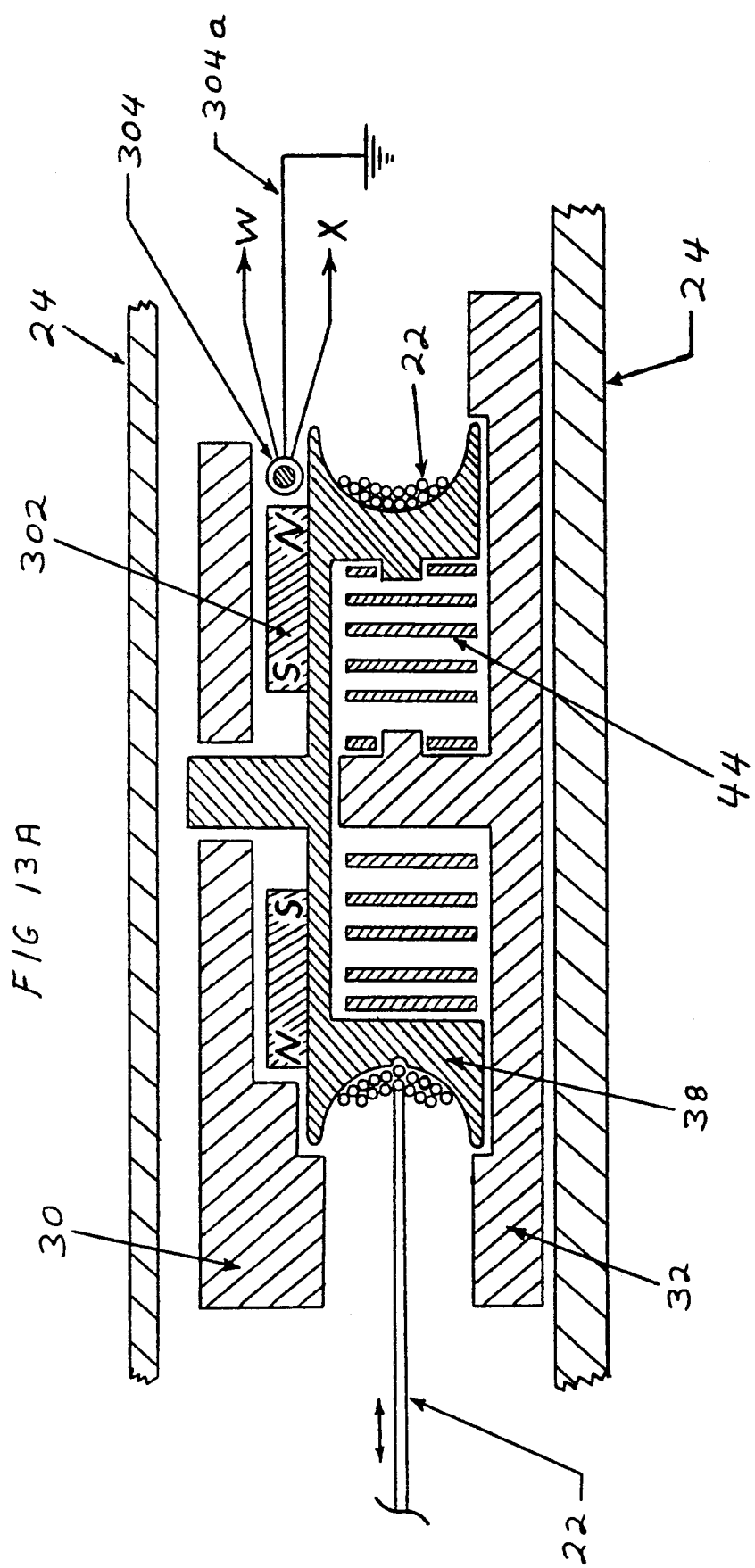
FIG. 13a is a vertical cross-section of the embodiment of FIG. 13.

Magnetic induction sensor 300 is mounted in place of mechanical sensing arm 50 (FIGS. 3 and 5). Thus, referring to FIG. 3, whereas the mechanical embodiment shown therein includes a metal sensing arm 50 mounted between barrel 38 and bracket 30, the magnetic induction embodiment includes a circular concentric magnet (FIG. 13) fixedly mounted to barrel 38 for rotation therewith. The configuration of the magnet is shown most clearly in FIG. 13a. An outer diameter of magnet 302 is magnetized to magnetic north, whereas an inner diameter is magnetized to magnetic south.

Referring next to FIG. 5, whereas the mechanical embodiment includes a pair of electrical terminals 64 and 66 positioned within the path of sensing arm 50, the magnetic induction embodiment replaces terminals 64 and 66 with a magnetic induction coil 304 positioned in close spaced relationship from the exterior radius of magnet 302. With this configuration, rotation of barrel 38 (FIG. 3), caused by displacement of wire 22, causes a rotation of magnet 302 with respect to magnetic induction coil 304. Accordingly, a current is induced in coil 304 which is conducted into shallow breathing indicator 200 via paths 207 and 209.

A microprocessor, similar to CPU 1 of FIG. 7, is provided within breathing indicator 200. This microprocessor is preprogrammed with algorithms in its ROM for detecting apnea and shallow breathing in response to electrical signals received along lines 207 and 209. In addition to recording a binary indication of each breath, rolling memory and shallow breathing indicator 200 may be preprogrammed to additionally record volumetric breathing information. Such information is not available using the purely mechanical embodiment, which merely provides a signal whenever the sensing arm contacts one of the sensing posts. However, with magnetic induction sensor 300, the degree and rate of expansion or contraction of the chest of the patient may be detected and recorded via detection of the amount and rate of rotation of magnet 302. In other words, magnet 302 rotates or pivots only slightly for shallow breaths, and pivots or rotates to a substantially greater extent during deep inhalations and exhalations. By recording an electrical signal representative of the degree and rate of rotation of magnet 302, algorithms preprogrammed within breathing indicator 200 can calculate the volume and duration of each breath. Algorithms for performing such computations are entirely conventional and will not be described in further detail herein, other than to indicate that, depending upon the algorithm, apnea monitor 10 may require calibration at manufacture to correctly calculate breathing volume.

Preferably, magnet 302 has an outer diameter of about 0.450-inch, a height or thickness of about 0.060-inch, and an inner diameter of about 0.150-inch. Magnetic induction coil 304 is mounted adjacent to the outer diameter of magnet 302 with a 0.010-inch gap, per FIG. 13a.

Summarizing the magnetic induction embodiment, a microprocessor within shallow breathing indicator 200 includes an internally-set time limit corresponding to a 35-second delay for comparing with signals received from the magnetic induction sensor. The internal time reference clock within the microprocessor is preferably crystal-driven. The microprocessor directly activates the pulsing piezoalarm such that there is no need for transistors Q1 and Q2 of FIG. 6. Moreover, transistor Q3 of FIG. 6 is also not required, since SCR1 of the magnetic induction embodiment automatically activates event indicator 208 via resistor 306, preferably having a resistance of 30 kilohms. The piezoalarm 100a is active only during an apnea event or shallow breathing, whereas flashing indicator 208 remains active until reset via switch S3. The pulsating piezoalarm 100a is activated via high output from pin or terminal T, as shown in FIG. 13. A high output from pin or terminal U activates LED 308, which specifically indicates periodic or shallow breathing. When such a condition is detected, both pins T and U are set to HIGH. Subsequent breathing motion detected via the magnetic induction sensor 300 automatically causes a reset of the piezoelectric alarm 100a, i.e., pin T is set to low by the microprocessor. However, the various LEDs are only reset by opening switch S3. Hence, pin or terminal P is tied to the low side of switch S3, to thereby reset periodic or shallow breathing LED 308 by switching pin U to a low state.

Inhalation causes a positive voltage across wires 207 and 209, whereas exhalation causes a negative voltage. Of course, the voltage bias may be reversed, as desired. Moreover, however, the amplitude of voltage generated across magnetic induction coil 304 depends upon the volumetric rate of breathing. Deep, quick breathing results in a long, fast rotation of magnet 302, thus generating higher voltage across induction coil 304 for a longer time. To determine breathing volume, the microprocessor merely integrates the generated voltage rate of change with respect to time, then employs empirically-determined factors to properly calibrate the breathing volume. Note that the induction coil 304 is center tapped to a ground, via path 304a, thus providing a proper voltage referenced to the microprocessor. The resistance of coil 304 need not be high, since the microprocessor within breathing indicator 200 does not provide a significant load to the coil. The total coil resistance should be about 2 kilohms with an inductance of about 0.2 millihenry.

Here, as in the mechanical embodiment described above, pins I and J provide output ports for serial downloading of a rolling memory CMOS static RAM. Thus, downloaded data stored within the RAM will show the breathing activity for a period of two minutes before an event and one minute after the event, likewise for an episode of shallow breathing. Of course, the microprocessor must be programmed to stop updating the CMOS static RAM after an event, such that that data will not be replaced by subsequent data. The amount of data storable within the CMOS static RAM is determined by the available memory within the RAM.

In the mechanical rotary slide switch embodiment, pin T (line 213), is normally high and only swings low when periodic or shallow breathing has been detected. When pin T goes low, a current path is opened for activating the piezoalarm and for activating the alternating flashing event indicator LEDs. The single LED 236 for periodic breathing also lights, thus differentiating this alarm mode from a simple apnea alarm. Switch S3 resets all LEDs.

In the magnetic induction sensing embodiment, pin T is normally low, then swings high when an apnea event or periodic breathing is detected, thus driving the piezoalarm directly. The alternating flashing LEDs in the event indicator automatically activate whenever the piezoalarm activates. Pin U is normally low, but is caused to switch high only when periodic breathing is detected, thus activating the separate periodic breathing LED 308 to differentiate this alarm mode from simple apnea. As with the mechanical version, switch S3 must be pressed to reset all LEDs.

Microcontrollers suitable for use as the CPU of the breathing indicator include the following: 80C31, 8031, 80C32, 8051, 8051AH, 80535, 80C51FH, 80C52, 80C552, 83C51FB, 8031AH, 80031, 80C51FC, 80C51FA, D55000, 80C537, and 80C535.

In both embodiments, the total nominal current draw with all alarms off is about 80 microamperes. By providing a 190-milliampere/hour capacity lithium cell, such as Eveready ® Part No. CR2032, 2000 hours of continuous use is allowed, or about one year of normal use.

What has been described is a self-contained, noninvasive apnea and shallow breathing monitor, which has no external electrodes or loose wires. The monitor is merely wrapped around the abdomen or chest of a patient, typically an infant, and activated. The monitor passively detects apnea events or shallow breathing and provides a loud audible warning to alert a parent or caregiver and possibly to awaken the patient, such that the patient may resume normal breathing. The monitor is totally waterproof and can be sewn permanently or temporarily into a favorite sleep garment of a child or infant, such that it need not be wrapped around the patient prior to sleep. Because it is totally waterproof, the monitor may be placed in a washing machine along with the favorite sleep garment onto which it is sewn. The monitor can also be looped into the garment, and pulled out prior to washing, as one would a normal leather belt.

The apnea monitor is self-adjusting to fit any infant, such that it can be stretched by a desired amount while mounting to a patient without requiring any recalibration. The monitor is self-evaluative by providing visual indications of moisture penetration, low battery voltage, or wear and tear on the Teflon TM -coated components. However, significant wear on the Teflon TM -coated components is not anticipated until after eight to ten years of use. A number of LEDs of various colors are illuminated to provide the parent or caregiver with a visual indication of the status of the monitor. Memory output is available for providing a serial downloading of recorded breathing data prior to and following an abnormal breathing event. The apparatus to receive and process the downloaded data is not described herein, since the apnea monitor is compatible with most PCs.

The electronic components are preferably formed on a single chip of silicone in die form utilizing conventional "blob-top" construction. Such a construction provides greater circuit protection and takes up minimal space.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A monitor for monitoring a patient to detect one of an apnea event and shallow breathing and for providing an indication responsive thereto, the monitor comprising:

belt means for substantially encircling a portion of the body of a patient and for expanding and contracting in response to respiration of the patient, said belt means including a flexible material;

detection means connecting first and second ends of the belt means for detecting expansion and contraction of the belt means;

the belt means including a substantially inextensible biased wire extending along at least a portion thereof, the wire having a first end displaceably connected to the detection means and a second end fixedly connected to the belt means at a location intermediate the first and second ends of the belt means, the wire being displaced from the detection means upon an expansion of the belt means, the wire being biased to return to a predisplaced configuration upon contraction of the belt means, with the detection means detecting respiration by detecting displacement of the wire;

a housing member enclosing the wire, said housing members insulating the sire from the flexible material and ensuring free and smooth displacement of the wire so that detection of respiration is not impeded;

measurement means for measuring a time interval between displacements of the wire; and determination means and indication means for, respectively, determining and indicating whether said time interval exceeds a minimum threshold time interval such that an indication is provided of a prolonged period without any detected respiration.

2. The monitor of claim 1, wherein the wire extends along substantially the length of the belt means to thereby substantially encircle a portion of the patient.

3. The monitor of claim 2, wherein an interior surface of the spring is coated with a low friction coating, such that wire slides easily within the spring as the spring expands and contracts.

4. The monitor of claim 3, wherein the low friction coating is polytetrafluorethylene.

5. The monitor of claim 2, wherein the housing member is a spring and wherein the belt means comprises an elastic fabric belt with the spring being carried within a conduit of the belt.

6. The monitor of claim 1, wherein the housing member is a helical spring and the wire is carried within the helical spring having a first end fixedly connected to the detection means and a second end fixedly connected to the belt means at a location intermediate the first and second ends of the belt means.

7. The monitor of claim 6, wherein the wire includes a low friction coating, the wire sliding easily within the spring as the spring expands and contracts.

8. The monitor of claim 7, wherein the low friction coating is a polytetrafluorethylene coating.

9. The monitor of claim 6, wherein the wire is coated with polytetrafluorethylene.

10. The monitor of claim 1, wherein a spring extends the length of the wire and substantially encloses the wire.

11. The monitor of claim 1, wherein the detector means includes biasing means for biasing the wire against displacement caused by expansion of the belt means, the wire returning to the predisplaced configuration upon a subsequent contraction of the belt means.

12. The monitor of claim 11, wherein the biasing means comprises a spring.

13. The monitor of claim 11, wherein the biasing means comprises a coil spring, the coil spring having an inner end mounted to an axial post and an outer end connected to the first end of the wire, the coil spring being oriented to provide a tension opposing displacement of the wire such that, upon displacement of the wire caused by expansion of the belt means, the coil spring winds thus providing a biasing tension so that, upon subsequent contraction of the belt means, the tension of the coil spring biases the wire to return to the predisplaced configuration.

14. The monitor of claim 13, the coil spring being enclosed within a bore within a rotatable member, the coil spring being attached to an inside surface of the rotatable member to thereby bias rotation of the member, the first end of the wire being attached to an outer surface of the rotatable member, a portion of the wire being wound around the outer surface of the rotatable member such that, as the belt means expands in response to inhalation, the wire unwinds from, and rotates, the rotatable member, thus causing the coil spring to wind within the rotatable member to provide biasing tension, and such that, as the belt means contracts in response to exhalation, the coil spring biases the rotatable member to rotate to a predisplaced configuration, with the wire being rewound thereon.

15. The monitor of claim 1, wherein the detection means comprises:

a displaceable member connected to the wire for displacement along a path in response to expansion and contraction of the belt means; and a sensing means for sensing displacement of the displaceable member along the path.

16. The monitor of claim 15, wherein the detector means further comprises a fixed member provided in the path of the displaceable member, and the sensing means comprises means for sensing contact of the displaceable member and the fixed member, the fixed member being provided within the path of the displaceable member such that the displaceable member and the fixed member are brought into contact upon one of a sufficient expansion and contraction of the belt.

17. The monitor of claim 16, wherein the sensing means further comprises electrical circuit means for providing a voltage potential between the displaceable member and the fixed member and for sensing contact of the displaceable member and the fixed member by detecting a drop in the voltage potential.

18. The monitor of claim 16, wherein the sensing means further comprises electrical circuit means for providing a voltage potential between the displaceable member and the fixed member and for sensing contact of the displaceable member and the fixed member by detecting an electrical current flowing between the displaceable member and the fixed member.

19. The monitor of claim 15, wherein the detecting means further comprises means for providing a magnetic field in the path of the displaceable member with movement of the displaceable member affecting the magnetic field and with the sensing means sensing the effect on the magnetic field.

20. The monitor of claim 15, the displaceable member comprising primary and secondary members;

the primary member being connected to the wire, the primary member being displaced along a path in response to expansion and contraction of the belt means;

the secondary member being frictionally mounted to the primary member, the secondary member being displaced along with the primary member, with the sensing means sensing contact only between the secondary member and the fixed member, and with the fixed member limiting displacement of the secondary member to a shorter path than the path of the primary member, the secondary member being displaceable only over a short path regardless of the amount of displacement of the primary member, to thereby enable detection of small expansions and contractions of the belt means following a large initial expansion caused by the belt means being expanded to fit a patient.

21. The monitor of claim 20, the primary member being a rotatable member, the displacement path of the primary member being an angular rotation path, the wire being attached to an outer circumferential surface of the rotatable member to cause rotation thereof in response to expansion of the belt means, the secondary member being disposed coaxially with the primary member against a side thereof and being displaceable therewith through a portion of the angular rotation path, the fixed member comprising first and second posts positioned within the rotation path of the secondary member to limit the angle of rotation of the secondary member such that, as the wire is displaced in response to respiration of the patient, the primary member rotates, with friction between the primary and secondary members causing the secondary member to likewise rotate and contact one of the posts of the fixed member.

22. The monitor of claim 21, the secondary member being confined between the side of the primary member and a fixed enclosure member, the secondary member abutting the enclosure member at a radial distance from the axis of the coil spring, the secondary member abutting the primary member at a larger radial distance from an axis of the coil spring such that, although friction between the secondary member and the primary member may be the same as friction between the secondary member and the enclosure member, the resulting torque acting on the secondary member is unequal, thus allowing the secondary member to be displaced along with the primary member while simultaneously being confined between the primary and enclosure members.

23. The monitor of claim 1, the indication means being an audible alarm.

24. The monitor of claim 23, the audio alarm being a piezoelectric transducer.

25. The monitor of claim 1, the indication means being a visible alarm.

26. The monitor of claim 1, the detection means, measurement means, determination means, and indication means being mounted to the belt means.

27. The monitor of claim 26, the detection means, measuring means, determination means, and indication means being provided within a housing.

28. The monitor of claim 27, the housing being water resistant.

29. The monitor of claim 28, the housing including means for indicating whether water has penetrated the housing.

30. The monitor of claim 1, the belt means being sewn onto a garment.

31. The monitor of claim 1, wherein at least one of the detection means, measurement means, determination means, and indication means is powered by a battery.

32. The monitor of claim 31 including means for indicating whether the battery has become spent.

33. The monitor of claim 1, wherein the detection means provides a signal responsive to detection of displacement of the wire, wherein the measurement means comprises:
  an RC circuit, a voltage means for charging the capacitor of the RC circuit, a means for receiving the signal from the detection means, and a means for discharging the capacitor upon receipt of the signal;
  wherein the determination means comprises means for comparing the voltage of the RC circuit to a reference voltage.

34. The monitor of claim 1, wherein the belt means comprises an elastic fabric belt having two connectable sections.

35. The monitor of claim 34, the two connectable sections being connected together with a plurality of mating hook and clasp members.

36. The monitor of claim 1, wherein the detecting means includes a means for detecting a period of shallow breathing.

37. The monitor of claim 36, wherein said means for detecting periods of shallow breathing includes a microprocessor means for receiving signals indicative of breathing and for calculating the total number and volume of breaths occurring during a period of time, and for comparing said number and volume with a minimum preprogrammed number and volume of breaths, said minimum number and volume of breaths being the minimum number and volume of breaths during said period of time below which hypoxia occurs.

38. The monitor of claim 1, wherein said wire is covered by a low friction coating, and wherein means are provided for detecting when a portion of said low friction coating becomes worn from said wire.

39. The monitor of claim 1, further provided with a rolling memory means for receiving data from said detection means representative of respiration and for storing said data as a function of time for a preselected time period.

40. The monitor of claim 39, wherein said rolling memory means is continuously updated until one of an apnea event and shallow breathing is detected, at which time said breaths are no longer overwritten.

41. The monitor of claim 40, wherein, when one of an apnea event and shallow breathing is detected, said rolling memory means stores data corresponding to breathing for a period of two minutes before the apnea event or shallow breathing until one minute after the apnea event or shallow breathing.

42. A respiration monitor comprising:
  belt means for substantially encircling a portion of the body of a patient and for expanding and contracting in response to respiration of the patient; and
  detection means connecting first and second ends of the belt means for detecting expansion and contraction of the belt means;
  the belt means including a substantially inextensible biased wire extending along at least a portion thereof, the wire having a first end displaceably connected to the detection means and a second end fixedly connected to the belt means at a location intermediate the first and second ends of the belt means, and a housing member enclosing the wire along a substantial portion of its length, said housing member isolating the wire from the belt means and ensuring free and smooth displacement of the wire so that detection of respiration is not impeded, the wire being displaced from the detection means upon an expansion of the belt means, the wire being biased to return to a predisplaced configuration upon contraction of the belt means, with the detection means detecting respiration by detecting displacement of the wire.

43. The apnea monitor of claim 42, further including:
  detection means for determining an apnea event;
  support means for mounting the detection means onto a patient; and
  alarm means for indicating an apnea event in response to the detection means, including a pair of alarm members that are sufficiently spaced apart around the patient to prevent sound blockage of both alarm members, both alarm members being simultaneously driven to provide a combined alarm sound.

44. A monitor for monitoring a patient to detect one of an apnea event and shallow breathing and for providing an indication responsive thereto, the monitor comprising:

belt means for contacting a portion of the body of a patient and for expanding and contracting in response to respiration of the patient;

detection means connected to the belt means for detecting expansion and contraction of the belt means;

the belt means including a wire member extending along at least a portion thereof, the wire member having a first end displaceably connected to the detection means, said belt means including a storage member rotatably winding a portion of the wire member for storage, and a second end fixedly connected to the belt means at a location offset from the detection means, the wire member being displaced from the detection means upon an expansion of the belt means, the wire member being biased to return to a predisplaced configuration upon contraction of the belt means, with the detection means detecting respiration by detecting displacement of the wire member;

measurement means for measuring a time interval between displacement of the wire member; and determination means for determining whether said time interval exceeds a minimum predetermined threshold time interval and, if so, providing a signal indicative of a prolonged time period without any detected respiration.

* * * * *